(12) United States Patent
Rohde et al.

(10) Patent No.: US 8,123,947 B2
(45) Date of Patent: Feb. 28, 2012

(54) PRIMING AND AIR REMOVAL SYSTEMS AND METHODS FOR DIALYSIS

(75) Inventors: Justin Rohde, Des Plaines, IL (US); Matthew Muller, Lindenhurst, IL (US); Alexander Braun, Milwaukee, WI (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 677 days.

(21) Appl. No.: 11/876,625

(22) Filed: Oct. 22, 2007

(65) Prior Publication Data

US 2009/0101576 A1 Apr. 23, 2009

(51) Int. Cl.
*B01D 61/24* (2006.01)
*B01D 61/32* (2006.01)
*B01D 61/34* (2006.01)
*B01D 63/02* (2006.01)
*B01D 63/16* (2006.01)

(52) U.S. Cl. ... 210/647; 210/646; 210/645; 210/321.71; 210/321.67; 604/5.01; 604/6.09

(58) Field of Classification Search .......... None
See application file for complete search history.

(56) References Cited

U.S. PATENT DOCUMENTS 250,868 A 12/1881 Abbott
(Continued)

FOREIGN PATENT DOCUMENTS

CH 296007 1/1954
(Continued)

OTHER PUBLICATIONS

Written Opinion of the International Searching Authority for International Application No. PCT/US2008/080166 mailed on Jan. 20, 2009.

*Primary Examiner* — Krishnan S Menon
(74) *Attorney, Agent, or Firm* — K&L Gates LLP

(57) ABSTRACT

A renal treatment fluid priming method includes priming an extracorporeal circuit connected to a patient with a physiologically compatible fluid, the extracorporeal circuit including an arterial line, a venous line and blood compartment of a blood filter; and pumping from a renal treatment fluid line in communication with the blood filter (i) pulling blood from the patient through the arterial line to flush the physiologically compatible fluid through the arterial line and the blood filter compartment into the renal treatment fluid line and (ii) pulling blood from the patient through the venous line to flush the physiologically compatible fluid through the venous line and the blood filter compartment into the renal treatment fluid line, such that a greater volume of blood is pulled from the patient via (i) and (ii) than a volume of the extracorporeal circuit.

23 Claims, 10 Drawing Sheets

U.S. PATENT DOCUMENTS

| | | |
|---|---|---|
| 927,476 A | 7/1909 | Barker |
| 1,505,050 A | 8/1924 | Lauritsen |
| 2,292,007 A | 8/1942 | Morgan |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,342,019 A | 9/1967 | Smythe |
| 3,412,760 A | 11/1968 | Franck |
| 3,527,572 A | 9/1970 | Urkiewicz |
| 3,581,464 A | 6/1971 | Bhuta et al. |
| 3,598,727 A | 8/1971 | Wilock |
| 3,677,710 A | 7/1972 | Hirsch |
| 3,744,492 A | 7/1973 | Leibinsohn |
| 3,756,234 A | 9/1973 | Kopp |
| 3,769,207 A | 10/1973 | Baer |
| 3,771,288 A | 11/1973 | Wisman et al. |
| 3,795,088 A | 3/1974 | Esmond |
| 3,827,561 A | 8/1974 | Serfass et al. |
| 3,830,234 A | 8/1974 | Kopp |
| 3,834,386 A | 9/1974 | Sisley |
| 3,849,071 A | 11/1974 | Kayser |
| 3,908,653 A | 9/1975 | Kettering |
| 3,946,731 A * | 3/1976 | Lichtenstein .................. 604/66 |
| 3,964,479 A | 6/1976 | Boag et al. |
| 3,976,311 A | 8/1976 | Spendlove |
| 3,985,134 A | 10/1976 | Lissot et al. |
| 3,996,027 A | 12/1976 | Schnell et al. |
| 4,031,891 A | 6/1977 | Jess |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,061,031 A | 12/1977 | Grimsrud |
| 4,102,655 A | 7/1978 | Jeffery et al. |
| 4,137,160 A | 1/1979 | Ebing et al. |
| 4,149,860 A | 4/1979 | Kulik |
| 4,151,088 A | 4/1979 | Wolf, Jr. et al. |
| 4,191,182 A | 3/1980 | Popovich et al. |
| 4,200,095 A | 4/1980 | Reti |
| 4,293,413 A | 10/1981 | Schnell |
| 4,304,670 A | 12/1981 | Watanabe et al. |
| 4,311,137 A | 1/1982 | Gerard |
| 4,325,715 A | 4/1982 | Bowman et al. |
| 4,332,264 A | 6/1982 | Gortz |
| 4,344,777 A | 8/1982 | Siposs |
| 4,345,919 A | 8/1982 | Wilkinson et al. |
| 4,345,999 A | 8/1982 | Sigdell et al. |
| 4,353,368 A | 10/1982 | Slovak et al. |
| 4,363,641 A | 12/1982 | Finn, III |
| 4,368,118 A | 1/1983 | Siposs |
| 4,427,009 A | 1/1984 | Wells et al. |
| 4,433,971 A | 2/1984 | Lindsay et al. |
| 4,464,172 A | 8/1984 | Lichtenstein |
| 4,486,188 A | 12/1984 | Altshuler et al. |
| 4,493,705 A | 1/1985 | Gordon et al. |
| 4,512,163 A | 4/1985 | Wells et al. |
| 4,531,937 A | 7/1985 | Yates |
| 4,568,333 A | 2/1986 | Sawyer et al. |
| 4,583,981 A | 4/1986 | Urquhart et al. |
| 4,586,925 A | 5/1986 | Carlsson et al. |
| 4,622,032 A | 11/1986 | Katsura et al. |
| 4,643,713 A | 2/1987 | Viitala |
| 4,643,715 A | 2/1987 | Isono et al. |
| 4,666,598 A | 5/1987 | Heath et al. |
| 4,681,606 A | 7/1987 | Swan, Jr. et al. |
| 4,722,725 A | 2/1988 | Sawyer et al. |
| 4,722,731 A | 2/1988 | Vailancourt |
| 4,734,269 A | 3/1988 | Clarke et al. |
| 4,806,135 A | 2/1989 | Siposs |
| 4,923,612 A | 5/1990 | Trivett et al. |
| 4,932,987 A | 6/1990 | Molina |
| 4,941,875 A | 7/1990 | Brennan |
| 4,946,439 A | 8/1990 | Eggers |
| D311,061 S | 10/1990 | Vrana et al. |
| 4,976,685 A | 12/1990 | Block, Jr. |
| 4,997,464 A | 3/1991 | Kopf |
| 5,047,147 A | 9/1991 | Chevallet et al. |
| 5,049,492 A | 9/1991 | Sauer et al. |
| 5,059,173 A | 10/1991 | Sacco |
| 5,061,236 A | 10/1991 | Sutherland et al. |
| 5,061,365 A | 10/1991 | Utterberg |
| 5,112,480 A | 5/1992 | Hukasawa |
| 5,167,921 A | 12/1992 | Gordon |
| 5,178,763 A | 1/1993 | Delaunay |
| 5,204,000 A | 4/1993 | Steadman et al. |
| 5,228,889 A | 7/1993 | Cortial et al. |
| 5,246,560 A | 9/1993 | Nekoksa et al. |
| 5,259,961 A | 11/1993 | Eigendorf |
| 5,268,077 A | 12/1993 | Bubik et al. |
| 5,328,461 A | 7/1994 | Utterberg |
| 5,336,165 A | 8/1994 | Twardowski |
| 5,356,376 A | 10/1994 | Milijasevic et al. |
| 5,358,481 A | 10/1994 | Todd et al. |
| 5,368,555 A | 11/1994 | Sussman et al. |
| 5,394,732 A | 3/1995 | Johnson et al. |
| 5,411,705 A | 5/1995 | Thor et al. |
| 5,421,815 A | 6/1995 | Noguchi et al. |
| 5,429,595 A | 7/1995 | Wright, Jr. et al. |
| 5,441,636 A | 8/1995 | Chevallet et al. |
| 5,468,388 A | 11/1995 | Goddard et al. |
| 5,484,397 A | 1/1996 | Twardowski |
| 5,489,385 A | 2/1996 | Raabe et al. |
| 5,490,925 A | 2/1996 | Eigendorf |
| 5,503,801 A | 4/1996 | Brugger |
| 5,509,895 A | 4/1996 | Noguchi et al. |
| 5,520,640 A | 5/1996 | Utterberg |
| 5,578,070 A | 11/1996 | Utterberg |
| 5,591,251 A | 1/1997 | Brugger |
| 5,605,540 A | 2/1997 | Utterberg |
| 5,637,081 A | 6/1997 | Noguchi et al. |
| 5,643,205 A | 7/1997 | Utterberg |
| 5,650,071 A | 7/1997 | Brugger et al. |
| 5,674,199 A | 10/1997 | Brugger |
| 5,681,294 A | 10/1997 | Osborne et al. |
| 5,683,355 A | 11/1997 | Fini et al. |
| 5,690,831 A | 11/1997 | Kenley et al. |
| 5,702,606 A | 12/1997 | Peter, Jr. et al. |
| 5,725,776 A | 3/1998 | Kenley et al. |
| 5,730,730 A | 3/1998 | Darling, Jr. |
| 5,763,266 A | 6/1998 | Palsson et al. |
| 5,776,091 A | 7/1998 | Brugger et al. |
| 5,776,345 A | 7/1998 | Truitt et al. |
| 5,800,597 A | 9/1998 | Perrotta et al. |
| 5,830,185 A | 11/1998 | Block, Jr. |
| 5,849,065 A | 12/1998 | Wojke |
| 5,851,202 A | 12/1998 | Carlsson |
| 5,858,239 A | 1/1999 | Kenley et al. |
| 5,863,421 A | 1/1999 | Peter, Jr. et al. |
| 5,895,368 A | 4/1999 | Utterberg |
| 5,902,476 A | 5/1999 | Twardowski |
| 5,910,252 A | 6/1999 | Truitt et al. |
| 5,928,889 A | 7/1999 | Bakich et al. |
| 5,931,990 A | 8/1999 | Andrews |
| 5,932,103 A * | 8/1999 | Kenley et al. ................. 210/646 |
| 5,948,251 A | 9/1999 | Brugger |
| 5,951,870 A | 9/1999 | Utterberg |
| 5,980,741 A | 11/1999 | Schnell et al. |
| 5,983,947 A | 11/1999 | Utterberg |
| 5,989,318 A | 11/1999 | Schroll |
| 6,010,623 A | 1/2000 | Schnell et al. |
| 6,019,824 A | 2/2000 | Schnell |
| 6,046,806 A | 4/2000 | Thompson |
| 6,051,134 A | 4/2000 | Schnell et al. |
| 6,053,967 A | 4/2000 | Heilmann et al. |
| 6,066,111 A | 5/2000 | Brockhoff |
| 6,071,269 A | 6/2000 | Schnell et al. |
| 6,117,342 A | 9/2000 | Schnell et al. |
| 6,132,616 A | 10/2000 | Twardowski et al. |
| 6,146,536 A | 11/2000 | Twardowski |
| 6,171,484 B1 | 1/2001 | Schnell et al. |
| 6,176,903 B1 | 1/2001 | Wamsiedler |
| 6,187,198 B1 | 2/2001 | Utterberg |
| 6,206,954 B1 | 3/2001 | Schnell et al. |
| 6,251,167 B1 | 6/2001 | Berson |

| | | |
|---|---|---|
| 6,274,034 B1 | 8/2001 | Nikaido et al. |
| 6,312,414 B1 | 11/2001 | Brockhoff et al. |
| 6,331,252 B1 | 12/2001 | El Sayyid et al. |
| 6,344,139 B1 | 2/2002 | Utterberg |
| 6,357,600 B1 | 3/2002 | Scagliarini |
| 6,391,541 B1 | 5/2002 | Petersen et al. |
| 6,391,638 B1 | 5/2002 | Shaaltiel |
| 6,464,878 B2 | 10/2002 | Utterberg |
| 6,481,455 B2 | 11/2002 | Gustafson et al. |
| 6,491,656 B1 | 12/2002 | Morris |
| 6,514,255 B1 | 2/2003 | Ferree |
| 6,537,356 B1 | 3/2003 | Soriano |
| 6,551,513 B2 | 4/2003 | Nikaido et al. |
| 6,558,340 B1 | 5/2003 | Traeger |
| 6,561,997 B1 | 5/2003 | Weitzel et al. |
| 6,562,107 B2 | 5/2003 | Purdom et al. |
| 6,572,576 B2 | 6/2003 | Brugger et al. |
| 6,582,604 B2 | 6/2003 | Nikaido et al. |
| 6,595,948 B2 | 7/2003 | Suzuki et al. |
| 6,755,801 B2 | 6/2004 | Utterberg et al. |
| 6,827,862 B1 | 12/2004 | Brockhoff et al. |
| 6,830,553 B1 | 12/2004 | Burbank et al. |
| 7,040,142 B2 | 5/2006 | Burbank |
| 7,087,033 B2 | 8/2006 | Brugger et al. |
| 7,097,690 B2 | 8/2006 | Usher et al. |
| 7,169,352 B1 | 1/2007 | Felt et al. |
| 7,186,342 B2 | 3/2007 | Pirazzoli et al. |
| 7,214,312 B2 | 5/2007 | Brugger et al. |
| 2001/0042441 A1 | 11/2001 | Purdom et al. |
| 2004/0019313 A1 | 1/2004 | Childers et al. |
| 2006/0213835 A1 | 9/2006 | Nimura et al. |

FOREIGN PATENT DOCUMENTS

| | | |
|---|---|---|
| DE | 1806654 | 5/1970 |
| DE | 3442744 | 6/1986 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 560368 A2 | 9/1993 |
| EP | 0 587 251 | 3/1994 |
| EP | 720856 A2 | 7/1996 |
| EP | 560368 B1 | 2/1998 |
| EP | 826383 A2 | 3/1998 |
| EP | 826384 A2 | 3/1998 |
| EP | 720856 B1 | 10/2001 |
| EP | 826384 B1 | 10/2001 |
| EP | 1323439 A2 | 7/2003 |
| EP | 1323439 A3 | 8/2003 |
| EP | 826383 B1 | 8/2004 |
| GB | 1 408 319 | 10/1975 |
| GB | 1 554 810 | 10/1979 |
| GB | 2 061 755 | 5/1981 |
| GB | 2 212 739 | 8/1989 |
| GR | 3026703 | 7/1998 |
| WO | WO 98/23353 | 6/1998 |

\* cited by examiner

PRIMING AND AIR REMOVAL SYSTEMS AND METHODS FOR DIALYSIS

BACKGROUND

The present invention relates generally to medical treatments. More specifically, the present invention relates to medical fluid treatments, such as the treatment of renal failure.

Hemodialysis ("HD") in general uses diffusion to remove waste products from a patient's blood. A diffusive gradient that occurs across the semi-permeable dialyzer between the blood and an electrolyte solution called dialysate causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, which has therapeutic benefits versus in-center hemodialysis treatments, which occur typically bi- or tri-weekly. Studies have shown that a patient receiving more frequent treatments removes more toxins and waste products than a patient receiving less frequent but perhaps longer treatments. A patient receiving more frequent treatments does not experience as much of a down cycle as does an in-center patient who has built-up two or three days worth of toxins prior to a treatment. In certain areas the closest dialysis center can be many miles from the patient's home causing door-to-door treatment time to consume a large portion of the day. HHD can take place overnight or during the day while the patient relaxes, works or is otherwise productive.

Controlling the flow of dialysate to and from the dialyzer (extracorporeal circuit) is important in HD (HF, HDF). It is important to know the overall flow volume of fresh fluid pumped through the dialyzer to know how much blood clearance or potential clearance has taken place over a treatment. It is also important to know the net overall flow volume difference of dialysate removed from the dialyzer versus the volume delivered to the dialyzer to know how much excess liquid or ultrafiltrate has been removed from the patient during a treatment.

In-center machines are sterilized or cleaned chemically, which allows balance chambers or other flow control apparatus to be reused. Certain home machines have instead used a disposable pumping cassette, which is used once and discarded. The cassette operates with pump actuators to control flow. The type of volumetric control dictates the type and complexity of the disposable cassette. It is desirable to use a type of volume control that makes the disposable cassette as simple and cost effective as possible.

SUMMARY

The present disclosure provides various medical fluid systems useful for any type of renal failure system, such as hemodialysis ("HD"), hemofiltration ("HF") and hemodiafiltration ("HDF"). The systems can also be used in any type of peritoneal dialysis ("PD") treatment. One system disclosed below provides a flow control system, which can be used to determine a total volume of fluid delivered to and from a dialyzer, extracorporeal circuit or patient's peritoneum, for example. The system provides fluid velocity sensors in the to- and from-dialyzer (patient) line, for example, measures ingoing and outgoing fluid flowrate, integrates the flowrate of fresh fluid delivered over the course of treatment to determine a total volume of fluid delivered to the dialyzer or patient. The system also integrates the flowrate of spent fluid removed from the dialyzer or patient over the course of treatment to determine a total volume of fluid removed from the dialyzer or patient. The system then subtracts the total volume of fluid delivered to the patient from the total volume of fluid removed from the patient to determine an amount of ultrafiltration removed over the course of treatment. The system can subtract the to-dialyzer (patient) flowrate from the from-dialyzer (patient) flowrate to determine a real time ultrafiltration ("UF") flowrate. The real time UTF flowrate is monitored to ensure that UF is not removed from the patient too quickly. Removing UF too quickly from the patient can have adverse effects on the patient.

The fluid velocity sensor in one preferred embodiment is a non-invasive sensor that does not need to contact the dialysis fluid to accurately detect flowrate. Suitable non-invasive fluid velocity sensors are discussed below but in many cases fall under one of the categories of optical, laser and heat pulse. The sensors in many cases include an emitter and a receiver, which are integrated into the dialysis instrument. When the disposable pumping cassette is placed into the instrument, a to-dialyzer (patient) flow sensing area of the cassette is aligned operably with a first emitter and receiver set, while a from-dialyzer (patient) flow sensing area of the cassette is aligned operably with a second emitter and receive set. The emitter and receiver can be provided on opposite sides of the cassette, e.g., one in the instrument door and one in the main area of the instrument. The emitter and receiver are provided alternatively on the same side of the cassette, e.g., both in the main area of the instrument.

The non-invasive flow sensors enable the system disposable to be relatively simple and cost effective. The system can employ peristaltic pumps, which require only a section of tubing to pump fluid. Such configuration is simpler than systems using membrane or volumetric pumps, which typically employ a disposable having a pair of rigid pump chambers and pump sheeting covering the chambers. The present system is also continuous (although peristaltic pumps have some inherent pulsatility), while the membrane or volumetric pumping systems using a set of membrane pumps operating out of phase with respect to each other can be somewhat less pulsatile.

The instant fluid cassette in one embodiment includes a rigid portion having flow sensing areas including flowpaths having known and controlled cross-sectional areas (e.g., square or circular), which can be located upstream or downstream of the associated dialysate pump. The fluid velocity sensors measure fluid velocity at the flow sensing areas. The system calculates flowrate knowing the sensed velocity and the cross-sectional area. Certain velocity sensors prefer strongly laminar flow. Thus it is contemplated to structure the flow sensing areas to create strongly laminar flow, which can be accomplished by structuring the flow sensing channel to have a Reynolds number less than one-thousand as discussed below.

The disposable cassette is connected fluidly to a pair of peristaltic pumping tubes, one for a to-patient (dialyzer) dialysate (infusate) pump and another for a from-patient (dialyzer) pump. In an HD, HF or HDF system, the disposable cassette can incorporate dialysate and blood hydraulics or just the dialysate hydraulics. In the former case, the cassette is connected to an additional peristaltic pumping tube for the blood pump. The cassette can include valve chambers, such as volcano type valve chambers. Alternatively, the system uses pinch clamps that clamp tubes leading to and from the cassette, such that the cassette does not incorporate the valving. The cassette can further include sensing areas for pressure sensors and other types of sensors, and other apparatuses, such as an air vent or filter and fluid heating pathway.

The HD, HF and HDF systems can use either one or both of heparin to prevent clotting and saline for priming and rinseback. It is accordingly contemplated to add third and fourth non-invasive fluid velocity sensors for the pumping of these fluids and corresponding flow sensing areas for heparin and saline in the cassette. Blood flowrate can be determined via the speed of the peristaltic blood pump since highly accurate blood flowrate information is typically not needed. It is contemplated however to add an additional non-invasive fluid velocity sensor and disposable flow sensing area for detecting blood flowrate.

As discussed above, in one embodiment the cross-sectional area of the flow sensing area of the cassette is provided via a rigid portion of the disposable cassette, so that the area is set. In another embodiment, which could be advantageous from a cost standpoint, the dialysis instrument forms a rigid clamshell of known cross-sectional area and sucks the cassette sheeting against the walls of the known volume clamshell during treatment to set the known cross-sectional area for flowrate determination. Such a configuration could be more repeatable from treatment to treatment because the system does not have to rely on manufacturing tolerances for the rigid portion. It may even be possible to eliminate the rigid portion of the cassette altogether. Here, a pneumatic source is used to suck the sheeting against the clamshell, which can make the use of pneumatic valves advantages because the pneumatic source is already present.

When controlling fluid balance and ultrafiltration, minimizing error in the differential flow measurement (difference between dialysate flow into and out of the dialyzer or patient) is more important than minimizing error in the absolute flow rates. The dialysate flow circuit in one embodiment removes error to due variation in the cross-sectional flow sensing area from the differential flow measurement, improving the accuracy of ultrafiltration determination over the course of a therapy. The accuracy improvement is achieved by incorporating a velocity sensor calibration bypass into the dialysate circuit. The bypass allows the fresh dialysis pump to pump dialysate past both the to- and from-patient (dialyzer) sensors, such that the sensors can be calibrated or set equal to each other assuming the same pump and same pump tubing pumping at the same speed will pump at a same flowrate past each sensor. Thus as long at the two sensors have the same error or no error, the ultrafiltration calculation should be accurate. Error does affect the total volume of fluid pumped to and from the patient or dialyzer however, so error is minimized as much as possible to better know and control the amount of toxin removed from the dialyzer or patient.

The bypass line is positioned in one embodiment from a junction between the first non-invasive fluid velocity sensor and the dialysate inlet to a junction between the dialysate outlet and the second non-invasive fluid velocity sensor. The line is valved such that the system includes a calibration mode (first valve state), in which in the bypass line is opened to calibrate the first and second non-invasive fluid velocity sensors and a therapy mode (second valve state) in which the bypass line is closed for treatment.

As discussed above, the system calculates flowrate from velocity and total volume from flowrate integrated over time. The system includes processing and software (sometimes referred to herein as a logic implementer) configured to perform these functions. It is contemplated to calculate the to- and from-volumes separately and subtract the to-volume from the from-volume to determine total ultrafiltration. Alternatively, for HD, HF and HDF, in which to- and from-flows are occurring at the same time, the logic implementer can instantaneously subtract the to-signal from the from-signal to determine a velocity delta and integrate the velocity delta over time to determine total ultrafiltration removed. In any case, integration can include determining a volume for each sample (velocity*area*sample time) and add each of the sample time volumes. Integration alternatively includes determining an average velocity or an average flowrate and multiplying the average value by the total time.

One non-invasive flow sensor suitable for use with the volume determination system discussed in detail below includes the placement of a pair of air detectors in the to- and from-dialysate lines. A source of sterile or clean air is connected to an air pump and to each of the to- and from-dialysate lines, upstream of the air detectors in each case. The air pump operates with system valves to selectively supply a bolus of air to the to- and from-dialysate lines. The air detector sensors of each pair sense the bolus of air as it travels by the air detectors at the same velocity as the fresh and spent dialysate. The time of travel between the air detectors is measured. The distance between the air detectors of both pairs is known. Distance and time yield velocity. Velocity and cross-sectional area of the fluid passage between the air detectors yield flowrate. Flowrate is integrated as discussed herein to yield to- and from-dialysate volume and ultrafiltration volume.

Various primary embodiments discussed herein involve priming of the extracorporeal circuit and dialysate circuit. One primary problem area for priming blood treatments includes the blood filter (dialyzer or hemofilter). The hollow fiber membranes tend to trap air bubbles. One system and method discussed below is configured to shake or vibrate the filter during priming to loosen or shake the bubbles free from the filter.

Another system and method discussed herein addresses a problem associated with priming the blood circuit with saline. After such priming, the saline is either pumped to the patient or to drain from the blood circuit. Either option is non-optimal as discussed below. The present system and method pumps the saline from the blood circuit, through the blood filter, to the dialysate circuit and to dialysate drain. Such action pulls blood from the patient into the primed blood circuit. The blood is then circulated for treatment.

Another system and method discussed herein incorporates a nozzle or aspirator into a disposable line or cassette. The nozzle for example can be incorporated into a dialysate air trap, which can be formed as part of the disposable cassette. The nozzle or aspirator causes the dialysate to form a spray. Air tends to separate from the dialysate droplets of the spray, especially under negative pressure from a pump. The removed air is trapped in the air trap and vented from the chamber to atmosphere for example.

A further system and method discussed herein includes various patient and caregiver alarms that wake or alert a patient or caregiver in the event of a therapy alarm, without necessarily waking or alarming people nearby.

It is accordingly an advantage of the present disclosure to provide a dialysis system having a relatively simple and cost effective disposable cassette.

It is another advantage of the present disclosure to provide a dialysis system that uses velocity sensing to control dialysate flow, which uses non-invasive velocity sensors, such as air bolus sensors.

It is a further advantage of the present disclosure to provide a dialysate flow control system, which can be expanded to sense any one or more of heparin flowrate, saline flowrate and blood flowrate.

It is yet another advantage of the present disclosure to provide an improved blood therapy priming technique that helps to release air bubbles trapped in the dialyzer.

It is yet a further advantage of the present disclosure to provide an improved post-priming technique that safely pumps saline or other priming fluid to drain, such that the priming fluid does not have to be pumped to the patient.

It is still another advantage of the present disclosure to provide an air removal system and method that separates air from dialysate droplets caused via a nozzling of the fresh dialysate fluid, which system and method can be incorporated into a disposable cassette.

It is still a further advantage of the present disclosure to provide systems and methods for alerting or awaking a patient or caregiver with a therapy alarm without necessarily alarming or waking people nearby.

Additional features and advantages are described herein, and will be apparent from, the following Detailed Description and the figures.

DETAILED DESCRIPTION

Volumetric Control Via Fluid Velocity Sensing

Figure 1:
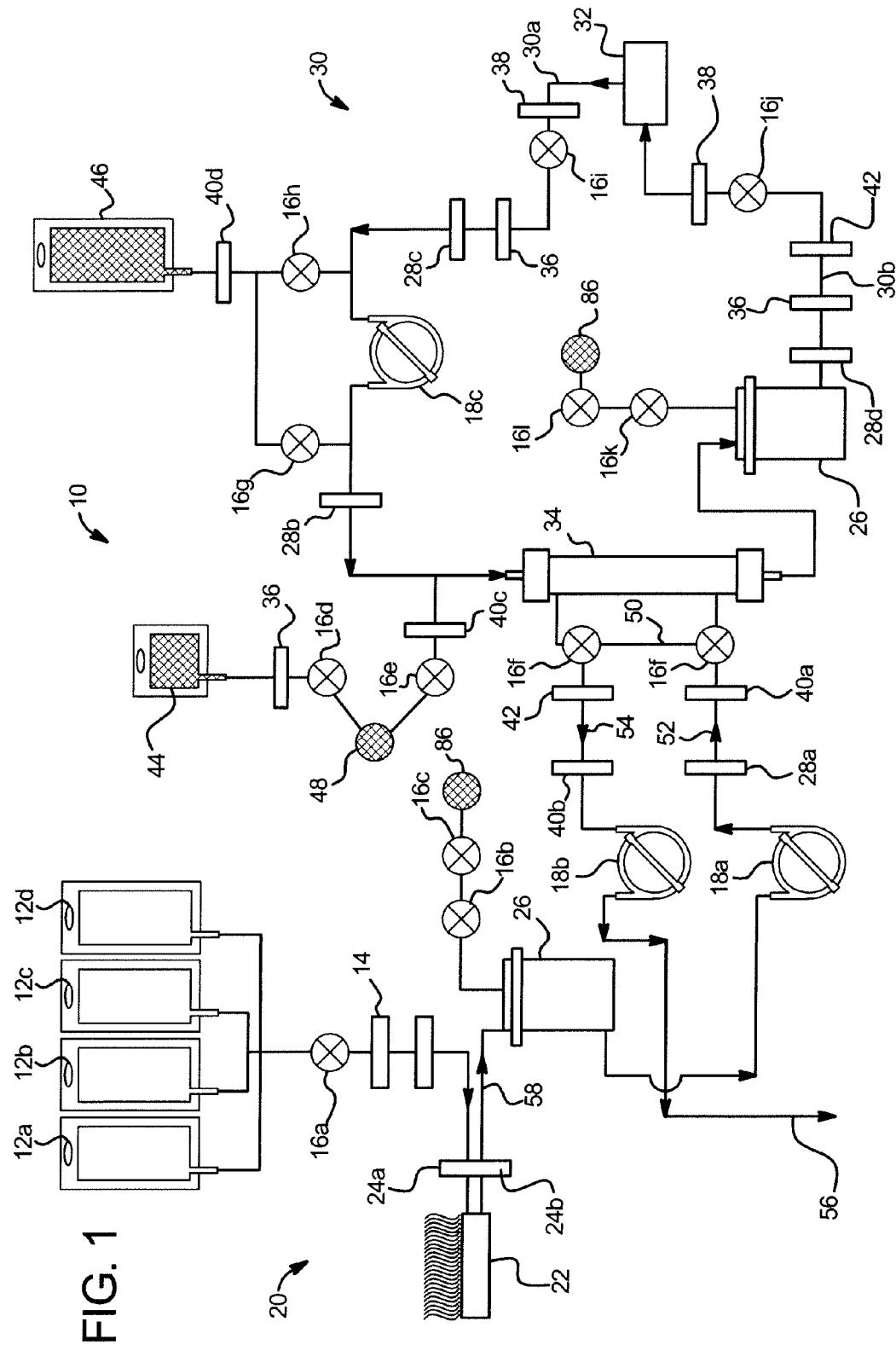
FIG. 1 is a schematic system view illustrating various embodiments for a non-invasive fluid volume and flowrate system for medical fluid treatments such as dialysis.

Referring now to the drawings and in particular to FIG. 1, system 10 illustrates one embodiment of a medical fluid system using the non-invasive flow sensing of the present disclosure. As discussed above, one application particularly well-suited for the non-invasive sensing of the present disclosure is a hemodialysis system, such as a blood cleansing system, e.g., hemodialysis or alternatively peritoneal dialysis, which uses the patient's peritoneal membrane as a filter to clean waste and impurities from the patient's vascular system. The flowrate sensing in the dialysis application is useful for multiple reasons. One reason is to integrate the flowrate of fresh dialysates to the patient or dialyzer over time, so that the total volume of fresh fluid delivered from the patient is known. One way to measure the effectiveness of a particular dialysis treatment is to monitor how much fresh fluid has been sent to the patient or dialyzer. Accordingly, the flow sensors are used to determine this value.

Another benefit of the non-invasive flow sensors is to also measure the amount of fluid removed from the dialyzer or patient. Typically, the amount of fluid removed from the dialyzer or patient is greater than the amount of fresh fluid delivered to the dialyzer or patient. This difference is known as ultrafiltration, which is important in dialysis because patients with failed kidneys retain liquid due to their inability to urinate. Dialysis removes such excess liquid from the patient, and it is important to know how much fluid has been removed. Dialysis patients have what is known as a dry weight. Upon beginning dialysis treatment, the patient is weighed to determine the volume of fluid that must be removed to return the patient to the patient's dry weight. Accordingly, it is important to track the total amount of ultrafiltration removed from the patient.

In a blood treatment setting, such as HD, HF or HDF, the non-invasive flowrate sensors can also be used to monitor how much heparin is delivered to the extracorporeal system and how much saline is used, for example, to prime or rinse back the extracorporeal system. As shown in detail below, the non-invasive flow sensing can be used to detect any one or more or all of the above-needed flowrates or total volumes.

System 10 includes a plurality of supply containers 12a to 12d, however, any suitable number of supply containers can be provided. Supply containers 12 (referring collectively to containers 12a to 12d in one embodiment) are dual chamber supply bags that are opened prior to treatment to allow different concentrates to mix prior to delivery to the patient. To ensure that properly mixed solution is delivered to the patient, system 10 includes a conductivity sensor 14, which monitors the conductivity of fluid exiting any of supply bags 12. By sensing conductivity, system 10 can determine whether properly mixed solution is traveling to the patient or whether pure concentrate is being delivered. System 10 includes a operation of various ones of valves 16 is described below.

System 10 is illustrated as a blood treatment system or hemodialysis system. Accordingly, system 10 includes a dialysate circuit 20 and a blood or extracorporeal circuit 30. Dialysate circuit 20 includes a fresh dialysate pump 18a and a spent dialysate pump 18b. Blood circuit 30 includes a single blood pump 18c. Pumps 18 (referring collectively to pumps 18a to 18c) are peristaltic pumps in the illustrated embodiment. Alternatively, pumps 18 are membrane-type pumps, positive displacement pumps, gear pumps or other type of pump. Peristaltic pumps are favored if they can be used because they operate with simple tubing and do not require disposable sheeting for operation as is the case with membrane pumps in a sterile environment. Peristaltic pumps are generally considered to be somewhat inaccurate however. In system 10, however, peristaltic pumps 18a and 18b are not relied upon for accuracy. Instead, the non-invasive flow sensors of the present disclosure monitor flowrate and overall volume of dialysate delivered via dialysate circuit 20.

Dialysate circuit 20 also has a dialysate heater 22. Heater 22 heats fresh dialysate for delivery to the patient. Temperature sensors 24a and 24b are provided to monitor the temperature of dialysate upstream and downstream of heater 22.

Both dialysate circuit 20 and blood circuit 30 include an air trap or air vent 26, which is configured and positioned to remove and/or trap air from the dialysate or blood, respectively. Air vents 26 operate with a plurality of vent valves 16 as illustrated. Circuits 20 and 30 each include at least one pressure transducer 28a to 28d (referred to herein collectively as pressure transducer 28).

Blood circuit 30 removes blood from patient 32 and pumps the blood through a dialyzer 34 as is known. Blood circuit 30 further includes a plurality of air detectors 36 and an access disconnection system or sensor 38. Dialysate systems 20 and blood circuit 30 further include blood sensors or blood leak detectors 42. Blood circuit 30 also includes a source of heparin 44, used to prevent blood clotting, and a source of saline 46, which is used for prime and rinseback.

Dialysate inlet line includes a first non-invasive flow sensor detector 40a. Dialysate outlet line includes a second non-invasive flow sensor or detector 40b. While dialysate inlet flow sensor 40a is shown downstream of fresh dialysate pump 18a, sensor 40a in an alternative embodiment is placed upstream of pump 18a. Further, while spent or outlet flow sensor 40b is shown upstream of spent dialysate pump 18b, sensor 40b in an alternative embodiment is placed downstream of spent pump 18b.

Fresh flow sensor 40a measures the flowrate of dialysate delivered to dialyzer 34. In a PD setting, non-invasive flow sensor 40a measures the flowrate of dialysate delivered to the patient's peritoneum. In one embodiment, as discussed in detail below, flow sensors 40 (referring collectively to sensors 40a and 40b) measure the velocity of fresh or spent dialysate, respectively. The velocity data is sent to a microprocessor operable with a memory that stores information concerning the cross-sectional area of the flow path operating with flow sensors 40. The processor and memory calculate flowrate using the sensed velocity and multiplying the velocity by the known cross-sectional area of the flow path. The flowrate data is then integrated or summed. For example, the processor can multiply each flowrate data by the processing sequence time to determine an infinitesimal volume of fluid pumped over the very short cycle time. The infinitesimal volumes are then added over the course of treatment to form an overall volume of fresh fluid delivered to the dialyzer or patient. This technique is illustrated in more detail below in the logic flow diagrams.

Spent dialysate flow sensor 40b performs the same flowrate and integration of volume of spent dialysate removed from dialyzer 34 or patient 32 as the case may be. The one or more processor then subtracts the total volume of fresh fluid from the total volume of spent fluid to determine an amount of ultrafiltration removed from the patient over the total course of treatment. This technique is illustrated in more detail below in the logic flow diagrams.

The totaling and subtraction of total volume can be performed continuously, periodically, or just at the end of treatment. For example, the ultrafiltration determination can be made every 10 minutes and compared to an expected amount of ultrafiltration. If the determined amount of ultrafiltration is, for example, less than the expected amount of ultrafiltration, the processing and memory of system 10 causes the speed of spent dialysate to pump 18b to increase. Additionally or alternatively, the processing and memory of system 10 slows fresh dialysate pump 18a. Both acts of either increasing spent dialysis pump 18b or decreasing the speed of fresh dialysis pump 18a result in a net gain in ultrafiltration rate. While decreasing the speed of fresh dialysate pump 18a may not be desirable from a total clearance standpoint, removing fluid too quickly from the patient via spent dialysate pump 18b can have a negative impact. It is therefore contemplated to set a maximum speed for pump 18b. Thus, if pump 18b is currently operating at its maximum desirable speed, fresh pump 18a may have to be slowed to achieve additional ultrafiltration.

System 10 can perform ultrafiltration profiling, in which the rate at which ultrafiltration is removed from the patient is varied over time according to a desired schedule. For example, a patient's ultrafiltration profile could begin with the ultrafiltration rate being set at a maximum speed and to decline thereafter linearly or step wise as treatment proceeds. In that profile, more total ultrafiltration is removed at the beginning of therapy then at the end, which can be desirable for certain patients. The profiles are generally developed over time after observing a patient undergoing dialysis treatment. Ultrafiltration profiles are more prevalent with blood based dialysis, such as hemodialysis, however, it is contemplated to use system 10 for peritoneal dialysis ultrafiltration profiling as well. To perform ultrafiltration profiling, the speeds of pumps 18a and 18b with respect to one another are adjusted as described above to achieve a desired ultrafiltration rate at a particular period of time during treatment.

Figure 2:
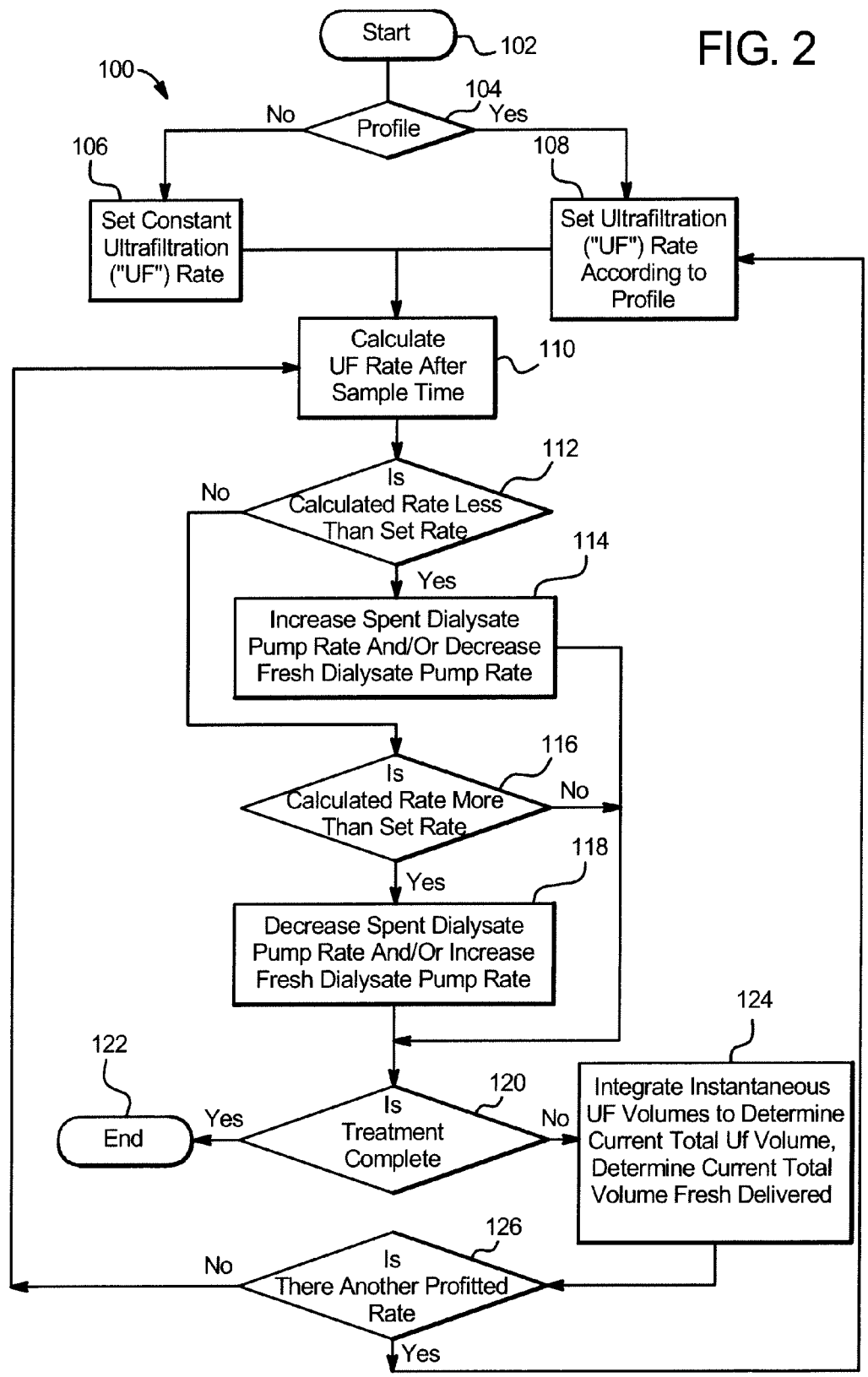
FIG. 2 is a logic flow diagram illustrating one method for determining fluid volume delivered and ultrafiltrate volume removed from non-invasive fluid velocity detection using the system of FIG. 1 for example.

Referring now to FIG. 2, method 100 illustrates one embodiment for determining ultrafiltration ("UF") rate in for either a constant rate or a varying UF rate profile. The steps or sequence of method 100 in an embodiment is stored on a microprocessor that can access one or more memory to run the method. Upon starting method 100 as seen at oval 102, method 100 first determines whether a profile of varying UF rates is too used as seen in connection with diamond 104. If no UF profile is to be used, method 100 sets the UF profile rate at a constant rate, as seen in connection with block 106. The constant rate is determined from the total UF volume, which is set before therapy knowing the patient's dry weight and the patient's weight at the time of therapy. Total treatment time is a desired total treatment time and is typically input into a dialysis device, such as an HD device, prior to beginning treatment.

Figure 3:
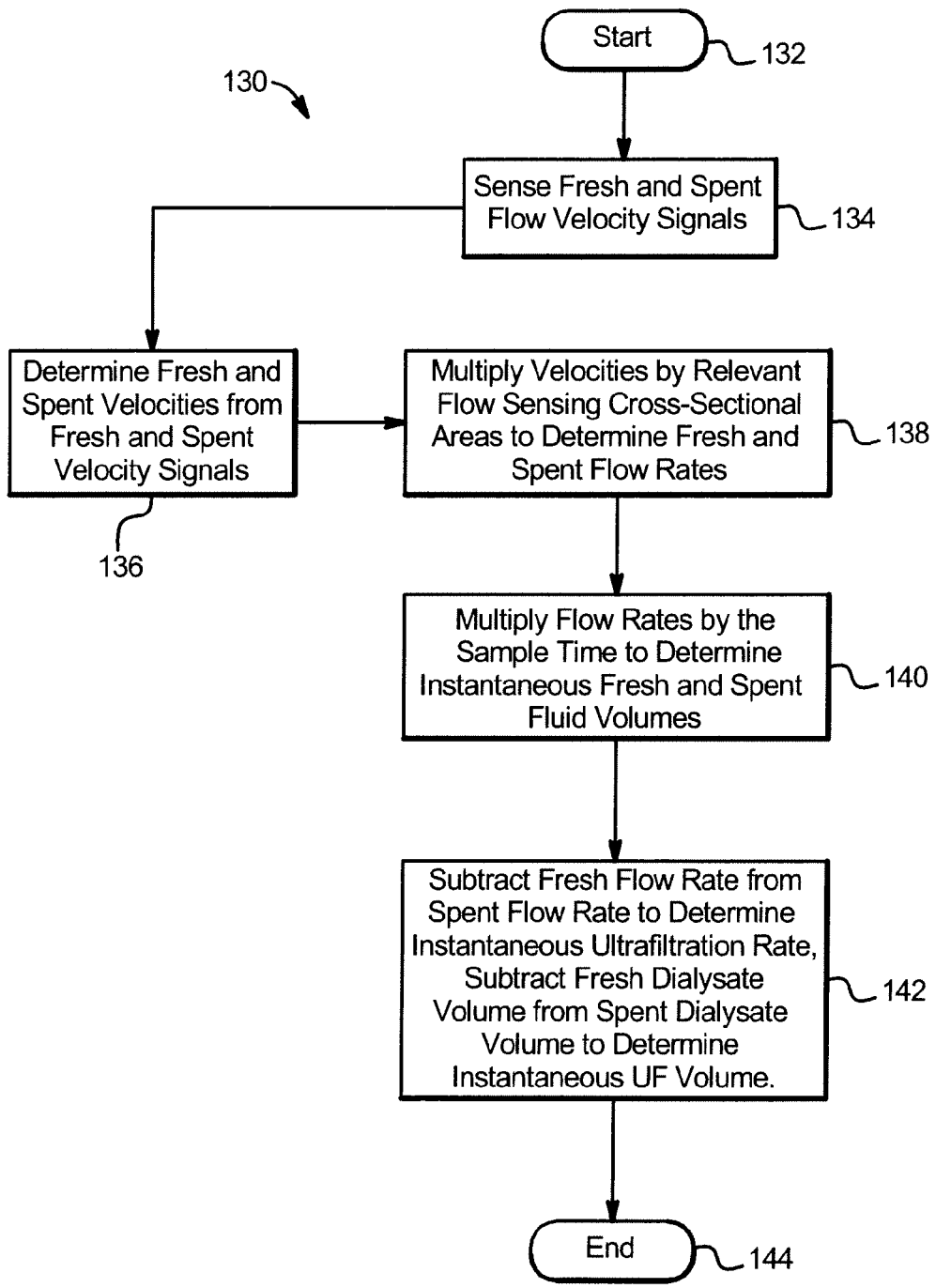
FIG. 3 is a logic flow diagram illustrating another method for determining fluid volume delivered and ultrafiltrate volume removed from non-invasive fluid velocity detection using the system of FIG. 1 for example.
Figure 4:
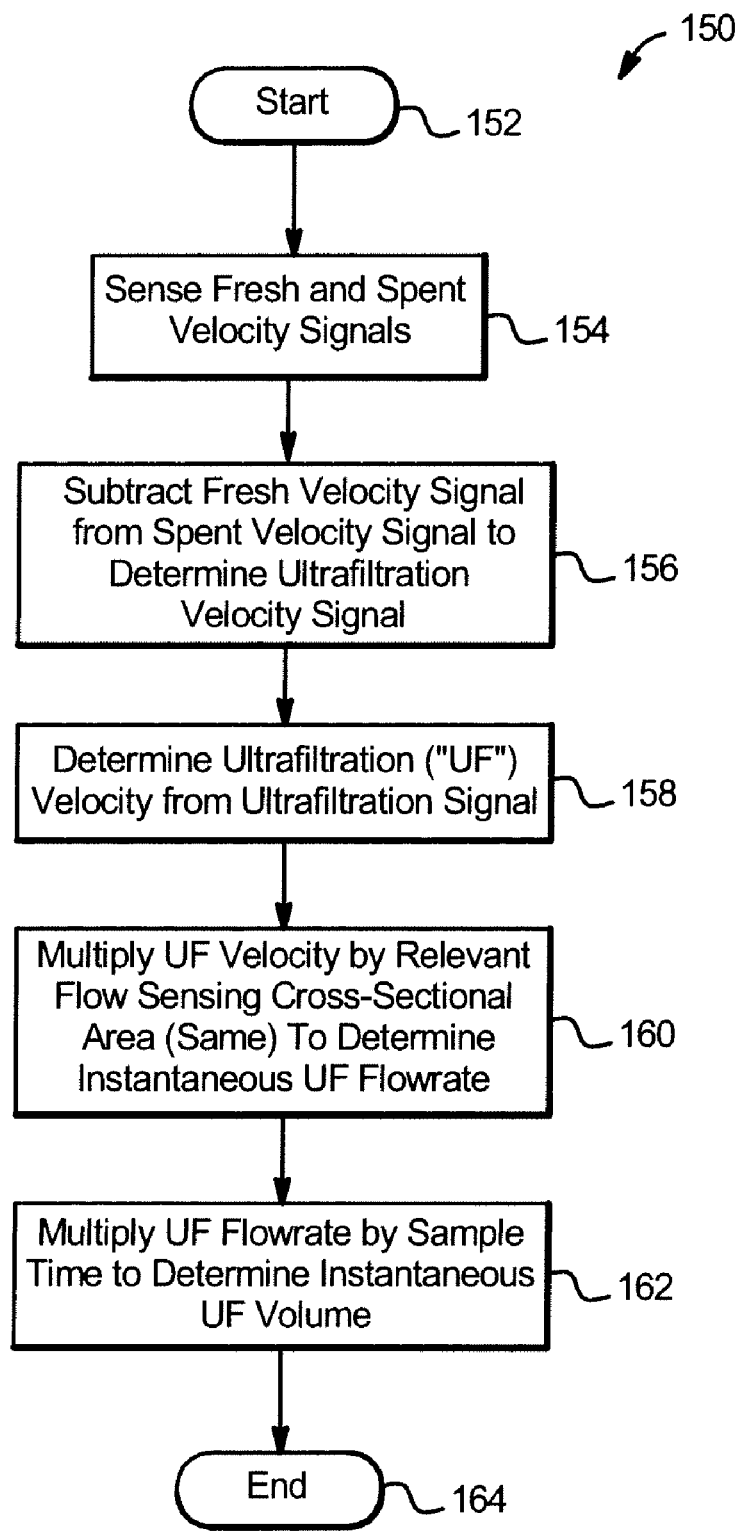
FIG. 4 is a logic flow diagram illustrating a further method for determining fluid volume delivered and ultrafiltrate volume removed from non-invasive fluid velocity detection using the system of FIG. 1 for example.

If a varying UF rate profile is used as determined in connection with diamond 104, method 100 sets the UF profile rate to a first rate of the profile, as seen in connection with block 108. In either case, at this point in method 100, the current UF rate is known. After treatment has begun, method 100 calculates an ultrafiltration or UF flowrate occurring over a sample time, as seen in connection with block 110. FIGS. 3 and 4 illustrate a plurality of methods for calculating instantaneous UF rate.

Method 100 then determines whether the calculated instantaneous UF rate is less than the currently set UF rate, as seen in connection with diamond 112. If the calculated rate is below the desired rate, method 100 increases the spent dialysate pump rate and/or decreases the fresh dialysate pump rate, as seen in connection with block 114, and as described above. In one embodiment, the spent or fresh dialysate pump is increased or decreased, respectively, via a set increment, e.g., a fraction of a rotation per second. Alternatively, the speed of the relevant pump is changed to a larger degree when the calculated rate is further away from the set UF rate. The speed of the relevant pump is changed to a lesser degree when the speed of the calculated UF rate is closer to the set UF rate. This is akin to a differential type of control.

If the calculated UF rate is not less than the set UF rate, as determined in connection with diamond 112, method 100 next determines whether the calculated instantaneous rate is greater than the set UF rate as determined in connection with diamond 116. If the calculated rate is more than the set UF rate, then the reverse of block 114 occurs, in which the spent dialysate pump rate is decreased and/or the fresh dialysate pump rate is increased, as seen in connection with block 118. The alternative embodiments discussed above in connection with block 114 for varying the pump flowrates are also applicable to the varying pump flowrates of block 118.

If the calculated instantaneous pump rate is the same as the set UF pump rate or after the either of the pump speed adjustments is performed in connection with blocks 114 or 118, method 100 next determines whether treatment is complete, as indicated at diamond 120. If treatment is complete, treatment ends as indicated in connection with oval 122. If treatment is not complete, method 100 integrates an instantaneous ultrafiltration volume produced according to the most recent instantaneous UF flowrate with a previous current UF volume to determine a new current total UF volume as seen at block 124 FIGS. 3 and 4 illustrate different methods for integrating UF volume. At block 124, method 100 also integrates an instantaneous volume of fresh fluid delivered to the patient/dialyzer with a current total fresh volume to determine new current fresh volume.

Next, according to diamond 126 method 100 determines whether the system should set a new ultrafiltration rate according to a profile of varying UF rates, if such a profile is being used. If a new rate is to be used, method 100 returns to the point of the method at step 108, at which a new ultrafiltration rate according to the profile is set. If in connection with diamond 126, either no profile is used or a profile is used but the UF rate does not change at the current time within treatment according to the profile, the method returns to the point of step 110 at which a new instantaneous UF rate is determined.

Referring now to FIG. 3, method 130 illustrates one embodiment for determining instantaneous UF flowrate and UF volume used above in connection with method 100 of FIG. 2. Upon starting method 130 at oval 132, a measurement from velocity sensors 40*a* and 40*b* is taken, as illustrated in connection with block 134. At block 136, the processing and memory storing method 130 and other appropriate data determines fresh and spent fluid velocities from fresh and spent velocity signals taken from sensors 40*a* and 40*b*. In an embodiment, the output signals from sensors 40 are voltage or current signals, and which can be analog or digital signals, such as pulse-width-modulated signals. The signals in one embodiment are correlated with velocity data stored in a memory operable with the processor running method 130. In this manner, a particular signal level from a sensor 40*a* or 40*b* corresponds to a particular velocity level or velocity for the fresh or spent flow paths, respectively.

Figure 5:
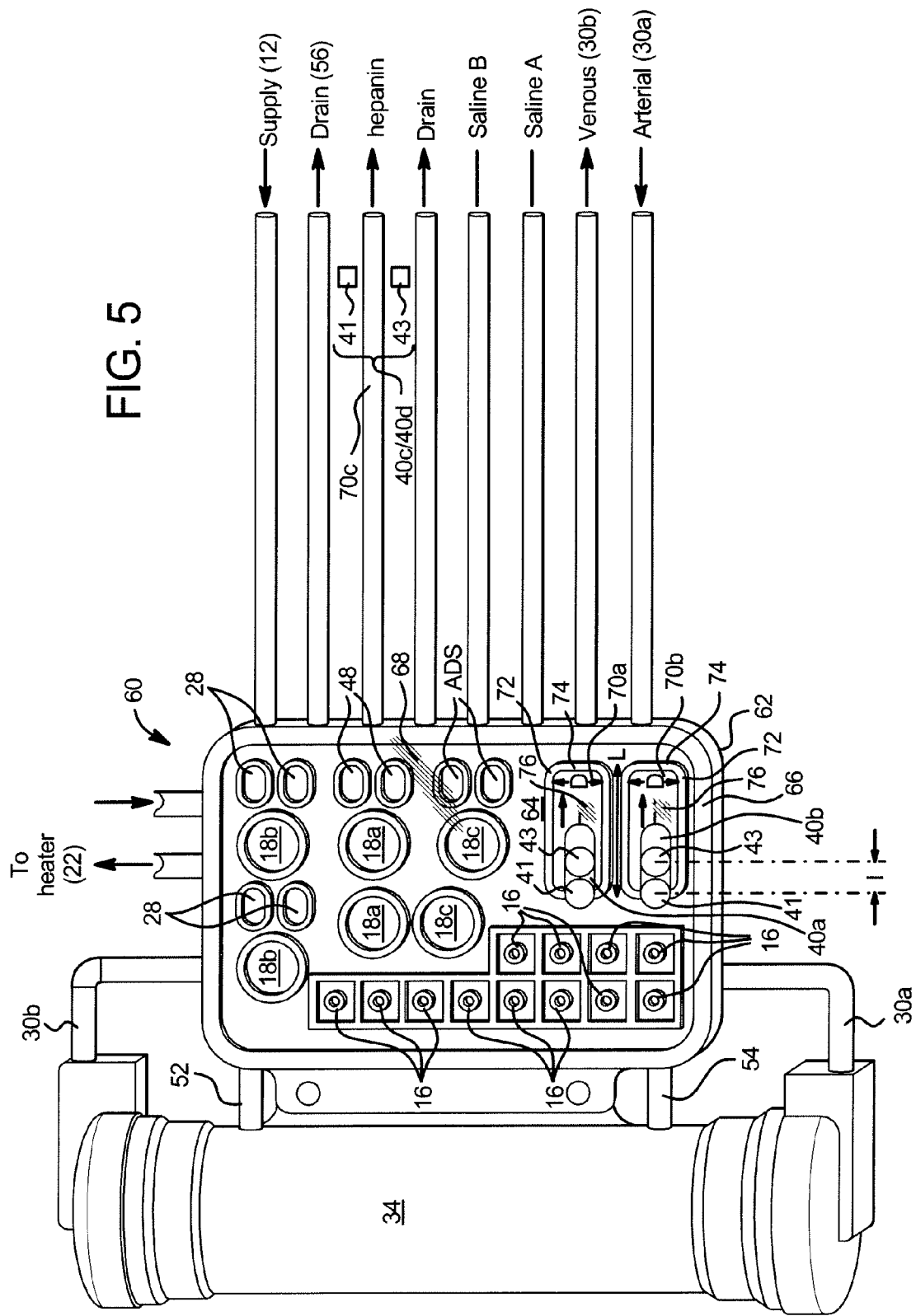
FIG. 5 is a perspective view of one embodiment of a disposable cassette configured to operate with the system disclosed in connection with FIG. 1.

In block 138, method 130 multiples the fresh and spent velocities by corresponding flow sensing cross-sectional areas to determine fresh and spent instantaneous flowrates. FIG. 5 illustrates one embodiment of a disposable cassette having flow sensing areas of a known cross sectional area. The sensors determine the fluid velocity in the flow sensing areas. The cross-sectional areas of the fresh and spent flow sensing areas are known. Accordingly, the instantaneous flowrates over the sample time for fresh and spent dialysate are determined using the sensed velocities and known cross sectional area.

In step 140, method 130 multiplies the fresh and spent flowrates by the sample time to determine instantaneous fresh and spent fluid volumes. Depending on the type of sensor used, the sample time can vary from milliseconds to seconds or even multiples of seconds, for example. Velocity is assumed to be constant over the sample time. Whatever the sample time, the flowrate determined over that sample time is multiplied by the sample time to determine an overall volume of fluid either delivered to the patient or dialyzer or removed from the patient or dialyzer during the sample time. The instantaneous volume determined in connection with block 140 is used, for example, at block 124 of method 100.

At step 142, method 130 subtracts the instantaneous fresh flowrate from the instantaneous spent flowrate to determine an instantaneous ultrafiltration rate. The method 130 also subtracts the fresh dialysate volume from the spent dialysate volume to determine instantaneous UF volume. The instantaneous UF volume is also used, for example, at block 124 of method 100. At oval 144, method 130 ends.

Referring now to FIG. 4, an alternative method for determining instantaneous UF rate, instantaneous UF volume and instantaneous volume of fresh fluid delivered. Upon beginning method 150 at oval 152, fresh and spent velocity signals are obtained from velocity sensors 40*a* and 40*b* as described above in connection with block 134 of method 130 as seen at block 154. At block 156, the fresh velocity signal is subtracted from the spent velocity signal to determine an instantaneous ultrafiltration velocity signal. Processing and memory in method 150 store a database that correlates the instantaneous ultrafiltration velocity signal to an instantaneous ultrafiltration velocity. That is, knowing the ultrafiltration signal level, method 150 finds an instantaneous ultrafiltration velocity corresponding to the determined instantaneous ultrafiltration signal level.

At block 160, the processor and memory multiply the instantaneous ultrafiltration velocity by the relevant flow sensing cross-sectional area to determine an instantaneous UF flowrate. In one embodiment, method 150 requires that the flow sensing cross-sectional area is the same in both the fresh and spent flow sensing areas. Indeed, in one implementation of method 150, the fresh and spent fluid sensing areas of the disposable cassette are exactly the same, at least as much as manufacturing tolerances will permit. Further, for both methods 130 and 150, the sample time for both fresh and spent instantaneous velocity signals is the same. The instantaneous UF flowrate determined in connection with block 160 can be used, for example, at block 110 of FIG. 2.

At block 162, method 150 multiples the instantaneous UF flowrate by the sample time to determine an instantaneous UF volume. The instantaneous UF volume in turn can be used at block 124 of method 100. At oval 164, method 150 ends.

As seen in FIG. 1, third and fourth velocity sensors 40*c* and 40*d* are positioned to sense the flow of heparin 44 and saline 46, respectively. The heparin circuit includes an air detector 36 placed upstream of valve 16*d*, which in combination with valve 16*e*, surrounds both sides of a mini-heparin pump 48. Pump 48 meters heparin 44 past flow sensor 40*c* into blood circuit 30 either continuously, semi-continuously or when needed. Heparin is an anti-coagulant, which helps prevent the patient's blood from clotting. Velocity sensor 40c can be used with a known cross sectional sensing area (e.g., of a cassette or tube) to provide heparin flowrate information. In one embodiment, heparin pump 48 operates in an open loop arrangement, in which it does not receive feedback. Here, flowrate data from heparin sensor 40c can be used with the processing and memory of system 10 to ensure that the flowrate of heparin is within an allowable range. Alternatively, processing and memory use the flowrate information from heparin flow sensor 40c to provide feedback information to heparin pump 48, such that the pump is sped up or slowed down in an attempt to achieve a desired heparin rate.

Fourth flow sensor 40d is placed downstream of saline supply 46. Saline 46 can be infused either upstream or downstream of blood pump 18c via valves 16h and 16g, respectively. In the illustrated embodiment, saline from supply 46 is fed into blood circuit 30 either by gravity or by the negative pressure generated by the rotation of blood pump 18c. Accordingly, flow sensor 40d in the illustrated embodiment is used to ensure that saline is flowing when needed and is flowing within a desirable range of flowrates. Velocity sensor 40d, as with velocity sensors 40a to 40c operates in an embodiment with a saline flow path of known cross sectional area, such that the velocity information gained from sensor 40d can be converted to flowrate data.

System 10 in one embodiment also includes a bypass and calibration line 50, which enables fresh dialysate flowing along dialysate inlet line 52 to flow through bypass line 50 instead of dialyzer 34. In this manner, the same flow through dialysate inlet line 52 and dialysate outlet line 54 is achieved. In an embodiment, bypass valves 16f are each three-way valves, which either allow fresh fluid to flow to dialyzer 34 or to bypass line 50 or to flow either from bypass line 50 or dialyzer 34 into dialysate outlet line 54. In an alternative embodiment, two 2-way valves can be used instead of a three-way valve 16f.

Flowing the same flow through both sensors 40a and 40b enables the sensors to be calibrated, such that for the same flow of fluid, the sensors output the same signal. As discussed herein, it is important that the overall amount of fresh fluid pumped to dialyzer 34 be known for clearance purposes. It is also important to know how much more spent fluid is pulled from the dialyzer 34 than fresh is delivered to the dialyzer 34. Thus, sensor 40b should read the same as sensor 40a.

Next, bypass line 50 is used to set sensor 40b to read the same as sensor 40a. Such procedure would provide accuracy in the differential flow measurement on the order of +/−0.1%, enabling both total volume and ultrafiltration goals to be achieved.

Referring now to FIG. 5, assembly 60 illustrates dialyzer 34 shown above connected to a disposable pumping cassette 62. Disposable pumping cassette 62 is alternatively separate from dialyzer 34. Cassette 62 includes a plurality of valve chambers 16, pressure sensing areas 28 and other sensor areas, which can be used for temperature sensing, air detection, blood leak detection or for the sensing of other parameters associated with a hemodialysis or peritoneal dialysis system. Cassette 62 on its reverse side includes flow paths that carry both dialysate and blood. Accordingly, cassette 62 is used for both dialysate circuit 20 and blood circuit 30. In an alternative embodiment, separate cassettes for dialysate flow and blood flow are provided. Cassette 62 is shown connected to a plurality of tubes, such as supply tubes connected to dialysate supplies 12a to 12d, a drain tube, and to- and from-heater tubes running to and from heater 22. Cassette 62 is also shown connected to a heparin or saline line. While a single line for either heparin or saline is provided, it should be appreciated that cassette 62 can include separate lines, one each for heparin and saline.

A portion of blood circuit 30 is shown, which connects dialyzer 34 to the blood flow pathways of cassette 62. Here anterial tube 30a extends from cassette 62 to dialyzer 34. Venous tube 30b extends from dialyzer 34 to cassette 62. Dialysate inlet line 52 and dialysate outlet line 54 are shown connecting the dialysate compartment of dialyzer 34 to dialysate pathways located on the reverse side of cassette 62. For example, bypass line 50 can be provided as a rigid fluid pathway on the reverse side of cassette 62.

In the illustrated embodiment, dialysate pumps 18a and 18b and blood pump 18c are shown as being membrane pumps. It is expressly contemplated to use sensors 40 alternatively with membrane or diaphragm type pumps. Cassette 62 could use peristaltic pumps, however, in which case, peristaltic pump tubes would form a u-shaped loop extending from cassette 62. The loops would wrap around peristaltic pumping heads of the dialysate and blood pump actuators located within the dialysis instrument. Cassette 62 in the illustrated embodiment includes a rigid base plate 64 and a rigid rim 66. Base plate 64 provides a base surface for valve chambers 16, pressure sensor areas 28 and other sensing areas shown on the illustrated side of cassette 62. Base plate 64 also provides the base for rigid flow paths located on the non-illustrated side of cassette 62. Cassette 62 includes sheeting 68 which is welded to either side of cassette 62, for example, to rigid rim 66. Sheeting 68 can additionally be welded to any of valve chambers 16, pressure sensing chambers 28 and the raised ridges of other sensors. Sheeting 68 can be provided on one or both sides of cassette 62. It should be noted that some of the cassette-based components shown in FIG. 1, e.g., flowpaths, sensing area, etc., are not seen in FIG. 5 because they are located on the opposite side of the cassette shown in FIG. 5.

Cassette 62 also includes flow sensing areas 70a and 70b, one each for velocity sensor 40a and sensor 40b. Flow sensing areas 70a and 70b can be provided in a number of different configurations depending on the configuration of velocity sensors 40. For example, velocity sensors 40a and 40b in FIG. 5 are provided on the same side of cassette 62 and are shown herein generally as an including emitter 41 and receiver 43. In an alternative configuration, receiver 43 is placed on the opposing side of the flow sensing area from emitter 41. In the configuration of sensors 40a and 40b illustrated, base wall 64 of cassette 62 can be used as one surface of flow sensing area 70a and 70b. Base wall 64 at areas 70a and 70b can be opaque or clear as needed for the particular type of emitter 41 and receiver 43 used. Ridges 72 and 74 extending from base plate 64 define the flow sensing areas 70a and 70b. If, for example, the flow of fluid travels in the direction of the arrows shown in the flow sensing areas, the cross sectional area is the height of raised ridges 72 and 74 multiplied by the distance D between longer ridges 72 of each of the flow sensing areas 70 (referring collectively to flow sensing areas 70a and 70b).

In an embodiment, flow sensing areas 70 are capped with a rigid plate 76 instead of flexible sheeting 68. Rigid plate 76 fixes the cross sectional area within flow sensing areas 70. Flexible sheeting 68 can be welded over rigid plate 76 or be welded around the flow sensing areas, e.g., to raised ridges 72 and 74. In an alternative configuration, emitter 41 and receiver 43 are positioned on opposite sides of cassette 62. In such a case, base wall 64 may not be provided within flow sensing areas 70. Instead, edges 72 and 74 of flow sensing areas 70 can extend can towards both sides of cassette 62 and be capped on both sides by a clear rigid plate 76. Clear materials for rigid portion 62 and plate 76 include acrylic, for example. Sheeting 68 in an embodiment is polyvinyl chloride ("PVC"). Again, flexible sheeting 68 can be applied on each side to rigid plates 76 or be welded around plates 76 as desired.

Velocity sensors suitable for system 10 are discussed below. Certain ones of those sensors may operate better with or even require laminar dialysate flow. It is therefore contemplated to employ one or more measure to make the flow of dialysate (fresh or spent) as laminar is possible through flow sensing areas 70. For example, based on the fluid viscosity, density, and maximum flowrate, the flow sensing lumen area 70 is in one embodiment structured to achieve a Reynolds number (Re) less than one-thousand. For example, the cross sectional area (width×height) of the flow channel is selected to achieve a Reynolds number less than 1000. Based on the resultant Reynolds number an Entrance Length ("EL") of the flow channel can be determined as shown below, to assure that laminar flow is established fully in the flow channel prior to the velocity. Total length of lumen 70 is the EL plus the length needed for sensing. For example, for flow sensing areas having non-circular cross-sections, the Reynolds number is defined as:

$Re = [\rho V D_h]/\mu$, in which $\rho$ is the fluid density,

V is the fluid velocity, $D_h$ is the hydraulic diameter, defined from the perimeter (P1) and area (A) of the cross-sectional flow sensing channel, $D_h = (4*A)/P1$, and $\mu$ is the fluid viscosity.

According to the above equation and knowing the fluid type and maximum fluid flowrate, a suitable cross-sectional area for the flow channel can be determined. The minimal length of the flow channel is driven by the entrance length effect. The entrance length effect defines the flow channel length required for laminar flow to be fully established in the flow channel prior to the sensor. A equation for Entrance Length ("EL") is roughly: $EL = 0.02*Dh*Re$. To assure that the fluid velocity measurement is taken in a region containing laminar flow, the measurement should occur at a distance equal to or larger than EL from the inlet of the flow channel.

Velocity sensors 40c and 40d in FIG. 5 illustrate that the sensors do not have to operate with cassette 62. Here, emitter 41 and receiver 43 of sensor 40c or 40d are placed on either side of the heparin or saline tube. The cross-sectional area is accordingly a function of the inner diameter of such tube. In one embodiment the tube s fixed so that it is not compressed or otherwise deformed so as to change the cross-sectional area from what is expected of a tube having a particular inner diameter. In another embodiment, the cassette walls or instrument walls are sized to have a fixed gap that compresses the tubing in a known and repeatable manner. The compression serves two advantages: (i) flattening of the tubing walls to improve tolerance in optical alignment for the heat pulse and other optical sensors listed above; and (ii) fixing the gap of the cassette or instrument helps to establish a consistent cross-sectional area. It is accordingly contemplated to splice in a rigid section 70c of tubing that forms a flow sensing area having a fixed and rigid cross-sectional diameter. Fixed section 70c in an embodiment is clear or transparent or is otherwise caused to have a desirable surface characteristic for the particular velocity sensor technology employed. Suitable materials for rigid flow area 70c include acrylic, ADS, polyurethane, polyethylene and polyvinyl chloride, for example.

Suitable sensors 40 for application within system 10 include a velocity sensor that is of a size sufficient to be incorporated within a dialysis instrument and pointed towards a flow sensing area (either on one side or two sides of the cassette), which flow sensing area can be on the order of less than a centimeter to a few centimeters in both L and D directions, although it may be necessary to provide a longer length in the flow sensing areas of up to or even surpassing ten centimeters. For the heat pulse sensor, the total distance 1 is longer than a shorter length L, which is the distance between the injection of the heat pulse and measurement of same. The additional distance of longer length L is to establish laminar flow prior to the heat pulse injection. Thus, total length L could be equal to or greater than 1+EL (discussed above). It is desirable to make L and D smaller if possible to minimize disposable size. Also, for the heat pulse sensors, it is desirable to make L and D smaller to minimize the conduction of heat out of the fluid prior to the heat pulse measurement site.

The velocity sensors in one preferred embodiment are non-invasive because it is desirable not to compromise the sterility of fluid flowing within cassette 62 or tubing section. Also, placing an invasive velocity sensor or flow sensor within the cassette or tube would likely require the placement of metallic and electronic apparatus within the cassette or tube, increasing the cost of the cassette. In many cases, cassette 62 and associated tubing are each discarded after a single therapy. Accordingly, it is desirable to limit construction of cassette 62 and associated tubing to inexpensive, polymeric materials that can be sterilized, e.g., via an ethylene oxide, gamma radiation or steam sterilization process.

One suitable, non-invasive velocity sensor is disclosed in U.S. patent application Ser. No. 10/786,562 (U.S. 2005/0005710, "the '562 application"), which is believed to be assigned to or under obligation to be assigned to Therafuse, Inc., located in Carlsbad, Calif. The non-invasive velocity sensor disclosed in the '562 application is a heat-pulse time of flight sensor. FIGS. 2, 3 and 4 of the '562 application each show a sensor having a plurality of heat sources located on one side of the flow sensing area (e.g., cassette or tube in the instant application) and a detector located on a second side of the known cross sectional flow sensing area. It is contemplated to use the '562 sensor with either cassette sensing areas 70a and 70b or a tubular flow sensing area 70c. In the cassette version, base wall 64 is not provided in the flow sensing area and instead rigid, e.g., acrylic plates are placed on either side of cassette 62 forming a rigid pathway between the plates. The heat sources of the time of flight sensor are located on one side of cassette 62, while a detector is located on the other side of the rigid flow sensing area.

In one embodiment, each heat pulse sensor uses one heat pulse laser diode (emitter), one red laser light emitting diode ("LED") and one photodiode operating with the red laser LED to form a detector. The heat pulse laser causes a local refractive index change in the fluid. The red LED/photodiode combination detects this local refractive index "downstream" from the heat pulse laser. For example, one of the heat sources or the detector could be mounted within the instrument, while the other of the heat sources and detector, whichever is more convenient to do so, is located in a door of the instrument, which encloses the cassette.

Other suitable, non-invasive velocity sensors may be found in the following references, the relevant portions of which are incorporated herein expressly by reference. The references include U.S. Pat. Nos. 4,654,803; 4,938,079; 6,386,050; 6,779,396 and 2003/0218738. Another suitable non-invasive velocity sensing system is disclosed in U.S. patent application Ser. No. 11/675,469 ("the '469 application"), entitled "Dialysis System Having Optical Flowrate Detection," filed Feb. 15, 2007, the relevant portions of which are incorporated herein by reference.

The velocity sensor of the '469 application, for example, looks for particles or air bubbles entrained in the fresh or effluent dialysate lines 52 and 54. One purpose of the '469 application is to detect air or fibrin in the flow path. As is known, it is desirable to eliminate air from dialysate circuit 20. Thus, the '469 system may not be suitable for flowrate detection if there is not a steady supply of air or particles to detect. It would, however, be a suitable flowrate system if enough particles existed to obtain an at least relatively steady sample of flowrate. An apparatus and method for injecting air into the system is discussed below, which injects a small amount of air into dialysate circuit 20 upstream and downstream of dialyzer 34 at known intervals. The air is sterile or otherwise sufficiently clean so as not to potentially harm the patient. The air is also removed from the system prior to reaching the patient or dialyzer.

Flow Velocity Sensing Via Air Injection

Figure 6:
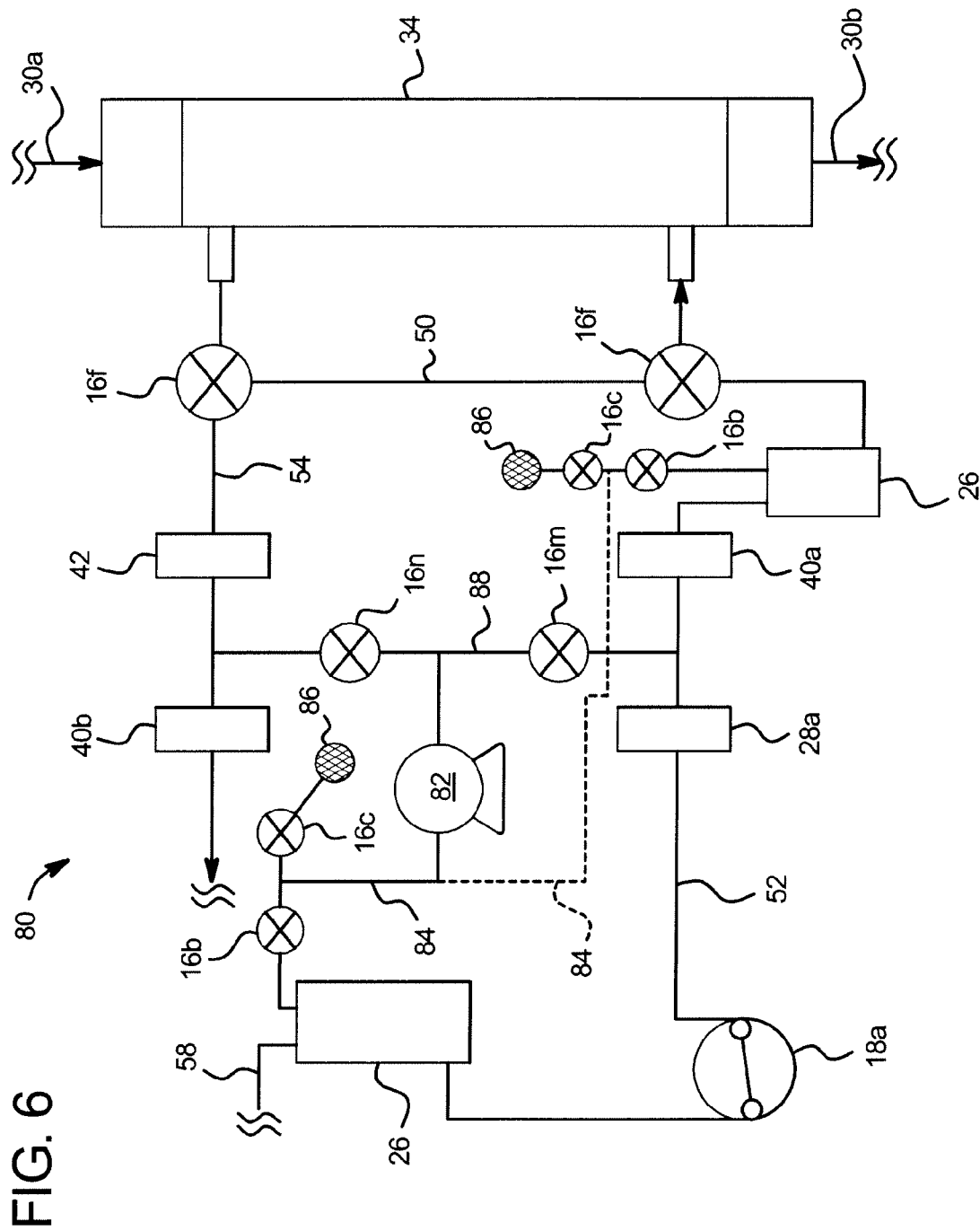
FIG. 6 is a schematic view illustrating various embodiments of a flowrate velocity sensor that injects boluses of air into the dialysate stream for fluid velocity detection.

Referring now to FIG. 6, system 80 illustrates one system and method for safely introducing small amounts of air into the dialysate stream for purposes of velocity and flowrate detection. System 80 includes each of the components and features of commonly numbered system 10. Additionally, system 80 includes an air pump 82 having an inlet line 84 connected between air purge valves 16b and 16c. Air purge valve 16c in turn is connected to a filter 86, which for example can be a 2.5 micron filter. Thus, system 80 has the option of opening vent valve 16b and pulling air from air trap 26 located upstream of fresh dialysate pump 18a. Alternatively, system 80 can close vent valve 16b, open vent valve 16c and pull air via filter 86, through valve 16c and inlet line 84, into and through air pump 82. In either case, only sterile or filtered air enters dialysate circuit 20.

Outlet line 88 from air pump 82 is connected via valves 16m and 16n to either dialysate inlet line 52 or dialysate outlet line 54, respectively. It should be appreciated that outlet line 88 connects to dialysate inlet line 52 upstream of velocity sensor 40a, such that one or more small bubbles of air can be introduced upstream of the velocity sensor. Likewise, air outlet line 88 feeds into dialysate outlet line 54 upstream of velocity sensor 40b.

The injection of air bubbles into spent dialysate line 54 does not raise a patient-air issue because those air bubbles are delivered to drain. The injection of air via air pump 82 into fresh dialysate line 52 may be done in such small quantity that the air is not harmful to the patient. This may be especially true in the case of HD, which is shown in FIG. 6 includes a dialyzer 34, which separates dialysate circuit 20 from the patient's blood. The membranes of the dialyzer 34 may prohibit any small amount of air from reaching the blood. With a PD system or in any case if the amount of air injected can be even potentially harmful to the patient, it is contemplated to add an additional air trap 26 as seen in system 80, downstream of fresh fluid velocity sensor 40a. Air trap 26 traps air injected into fresh line 52. Indeed, it is contemplated to replace air trap 26 upstream of dialysate pump 18a with air trap 26 downstream of sensor 40a. Here, air is drawn into air pump 82 via alternative air inlet line 84 shown in phantom. As before, air into alternative inlet line 84 can be drawn from air previously injected into fresh dialysate line 52 via air trap 26 by opening vent valve 16b. Alternatively, air is drawn through a filter 86 and open valve 16c into alternative air inlet line 84.

The '469 application referenced above discloses one suitable sensor for detecting air and determining flowrate assuming that the dialysate travels at the same velocity as the sensed air that the dialysate carries. In another embodiment, sensors 40 include a pair of air detection sensors, such as sensor 36, which can be a Lifeguard 200 or similar sensor provided by Zevex, Salt Lake City, Utah. The air sensors are spaced apart a known distance at a flow sensing area 70 of known cross-sectional area. The time between the detection of air flowing between the air detection sensors is noted. Fluid velocity is determined via the known distance and time. Flowrate is determined via the velocity and cross-sectional area. Flowrate is assumed to be constant until the next pair of readings is taken. Total fresh volume and UF is determined as described above.

While system 80 has been shown in use with a dialyzer 34, system 80 may be used alternatively for PD. Here, as above, dialyzer 34 is replaced with the patient's natural filter, the peritoneal wall. In most PD treatments, a single patient inlet/outlet tube is used. Here, a single set of ADS sensors can be used. Air trap 26 is placed between the point of injection into the patient line and the patient. Air does not have to be removed from effluent dialysate that is removed from the patient's peritoneum. While a single patient line is more prevalent for PD, system 80 can operate alternatively with dual patient line PD modalities. Here, the dialysate circuit is very similar to that of FIG. 6, but wherein patient 32 replaces dialyzer 34.

Priming Blood Circuit With Blood

Figure 7:
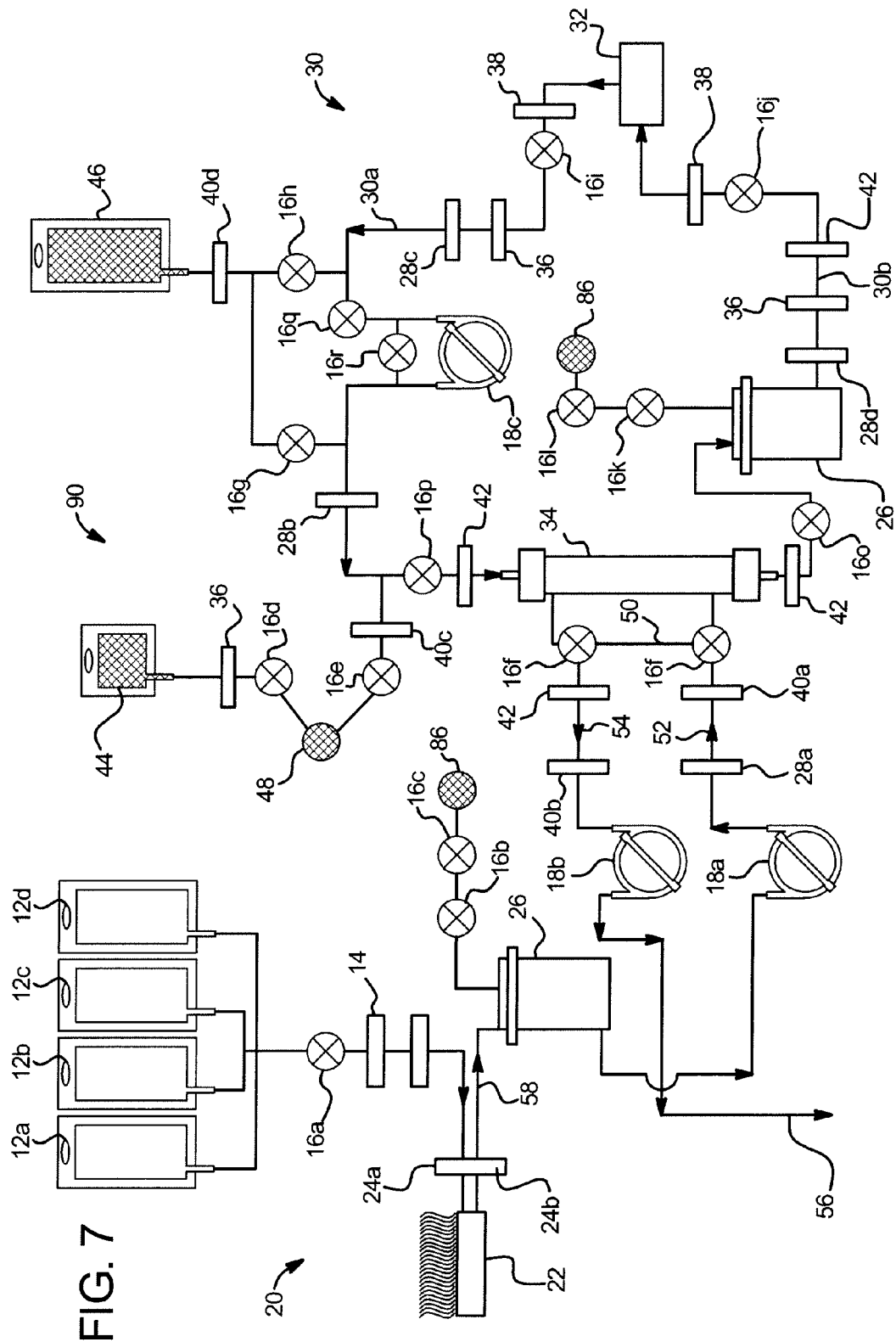
FIG. 7 is a schematic system view similar to that of FIG. 1, but which includes additional apparatuses for pumping priming solution to dialysate drain.

Referring now to FIG. 7, system 90 illustrates another system and method of the present disclosure. Known priming techniques for blood therapies such as dialysis have involved priming the blood circuit 30 with a physiologically safe fluid, such as saline. Once blood circuit 30 is primed, the saline needs to be displaced with blood. Known displacement techniques have either pumped the saline into the patient or pumped the saline to drain. Pumping the saline into the patient is not optimal because one of the goals of dialysis is to remove blood from the patient who may already be hyperpolemic. The saline adds additional fluid that needs to be removed. Pumping the saline to drain can be problematic if the patient or caregiver is not careful to prevent pumping the patient's blood to drain. The following system and method pump blood from the patient into both sides of blood circuit 30, which pushes the saline into the dialyzer and through the dialyzer membranes into the dialysate circuit. Once in the dialysate circuit 90, the system pumps saline safely to the dialysate drain.

In the following priming technique of system 90, it is assumed that both the dialysate circuit 20 and blood circuit 30 are primed fully. Dialysate circuit 20 can be primed with dialysate, e.g., up to valves 16f. The blood circuit 30 can also be primed with dialysate or can be primed with saline from saline source 46 through and including both sides of dialyzer 34. The arterial line 30a and venous line 30b are connected to patient 32 as seen in FIG. 1. Valve 16o added to venous line 30b of blood circuit 30 of system 90 just after the blood outlet of dialyzer 34 is closed, so that saline can be forced through the semipermeable membranes of the dialyzer, into the dialysate compartment of the dialyzer 34 and out dialysate outlet line 54. Valves 16p and 16q are also added to arterial line 30a for various embodiments discussed below.

In a first step, venous line valve 16j is closed, arterial line valve 16i is opened. Valve 16f in to-dialyzer line 52 is closed. Valve 16f in from-dialyzer line 54 is opened. Thus a fluid path from patient 32 to dialyzer 34 and from dialyzer 34 to dialysate drain 56 is open. Blood pump 18c pumps saline from the arterial line 30a into the blood compartment of dialyzer 34 pushes the saline through the semipermeable membranes within dialyzer 34 and out the dialyzer outlet and into from-dialyzer line 54. This action causes blood to be pulled from patient 32 and into the arterial line 30a of blood circuit 30. If the dialysate pumps 18a and 18b are peristaltic pumps, pump 18b is also used to pull the saline from dialyzer 34 to drain 56.

System 90 can determine when saline has been fully flushed from the arterial line of blood circuit 30 in a number of ways. In one way, system 90 knows that a number of strokes of blood pump 18c moves a certain volume of fluid equal to the volume in arterial line 30a. Even if all saline is not removed, removing most all the saline is still advantageous. Further, if an additional amount of blood is drawn into arterial line 30a and through dialyzer 34, the portion of the blood that is passed through the semipermeable membranes of the dialyzer is blood water or blood liquid. The platelets, red and white blood cells are too large to pass through the pores of the semipermeable membranes. In essence a small amount of ultrafiltration occurs. Thus it is not harmful to the patient to over pump blood to force saline out of dialyzer 34. Alternatively, an additional blood sensor 42 is placed at the inlet of dialyzer 34 to detect blood and stop blood pump 18c accordingly or soon thereafter.

After removing saline from arterial line 30a, system 90 cleans venous line 30b. Either dialysate return pump 18b or blood pump 18c can be used to pull saline through venous line 30b. Indeed, dialysate return pump 18b can be used in the first instance to clear the saline from arterial line 30a for example if blood pump 18c is provided instead in venous line 30b.

To use blood pump 18c to clean venous line 30b, valves 16j, 16o, 16p and 16f in return line 54 are opened. A valve 16q located on the patient side of blood pump 18c is closed. Blood pump 18c is run in the reverse direction from normal operation, pulling saline into dialyzer 34 and pushing the saline out dialysate return line 54 to dialysate drain 56. Here, dialysate return pump 18b operated run to push the saline to drain.

It may be advantageous to use dialysate return pump 18b alone to pull saline through venous line 30b. Here, valves 16j, 16o and 16f in return line 54 are opened, while valve 16p and valve 16f in to-dialysate line 52 are closed. Pump 18b is run, pulling saline through venous line 30b, dialyzer 34 and valve 16f in return line 54 to drain 56. That operation pulls blood from patient 32, through venous line 30b and into dialyzer 34. A bypass line controlled by valve 16r can be used so that peristaltic pump 18c does not have to be operated running spent dialysate pump 18b to pull saline and blood through arterial line 30a. Alternatively, the bypass line is not provided and blood pump 18c is run (at the same speed or slightly faster than the speed of spent dialysate pump 18b) when ridding arterial line 30a of saline. In any case, when using dialysate return pump 18b, (i) arterial line 30a can be cleaned first, then venous line 30b, (ii) venous line 30b can be cleaned first, the arterial line 30a, or (iii) both arterial and venous lines 30a and 30b can be cleaned simultaneously. Depending on the sequence, one or more or all of valves 16o, 16p and 16q may not be necessary.

Each of the same methods discussed above for knowing when saline has been fully flushed from blood circuit 30 is applicable to the draining and filling of venous line 30b. For example, blood pump 18c or dialysate return pump 18b can be run a number of strokes presumed to pull a volume of liquid equal to the volume of venous line 30b fully through dialyzer 34. Again, even pulling most of saline from venous line 30b is advantageous. Further, pulling more liquid than needed is permitted because this results in an ultrafiltration of liquid from the patient, which is a purpose of dialysis. Here, the system can be configured to pump a number of strokes sufficient to pull a greater volume of blood from the patient than the volume of the extracorporeal circuit 30 (including blood compartments of dialyzer 34) to ensure maximum saline clearance. Alternatively, a detector capable of distinguishing blood water from dialysate can be located in one/both of the dialysate lines 52 and 54 near dialyzer 34 to sense when blood water has cleaned the dialyzer and fully cleaned the blood circuit 30 of saline. In a further alternative embodiment, either one of blood leak detectors 42 could be optionally located on either end of dialyzer 34 could be used to detect blood and stop the saline rinse. Here, saline is cleaned from blood circuit 30 up to the dialyzer.

It should be appreciated that the fluid sensors 40 discussed above in connection with FIGS. 1 through 6 are not critical to the saline rinse system 90 just discussed. That is, system 90 could use balance chambers or other types of volumetric control rather than flow sensors 40 and still perform the method as discussed in connection with FIG. 7.

Priming Using Automated Mechanical Vibration

System 90 provides one method and apparatus for pulling saline from the primed blood circuit before beginning treatment. FIGS. 8 to 11 illustrate various apparatuses used during the initial fill of saline or other fluid needed to prime blood circuit 30. It is understood in the art that air needs to be purged from both dialysate circuit 20 and blood circuit 30 before beginning treatments. One problematic area in priming blood treatments is the priming of dialyzer or blood filter 34. Whether used for hemodialysis, hemofiltration, or hemodiafilttration filter 34 includes many very thin hollow fibers having pores sized to enable liquid from blood but not blood solids to pass from the inside of the hollow fibers to the dialysate portion of filters 34. The pores and tight spacing of the hollow fibers of filter 34 tend to trap small air bubbles. Further, the larger surface area and tight spacing of the thin hollow fibers also creates a surface tension sufficient to trap small air bubbles. Apparatuses 170, 180, 190 and 200 of FIGS. 8 to 11, respectively, agitate the dialyzer as it is being primed with saline or other fluid to dislodge the air bubbles from the hollow fibers within and inner wall of filter 34.

Figure 8:
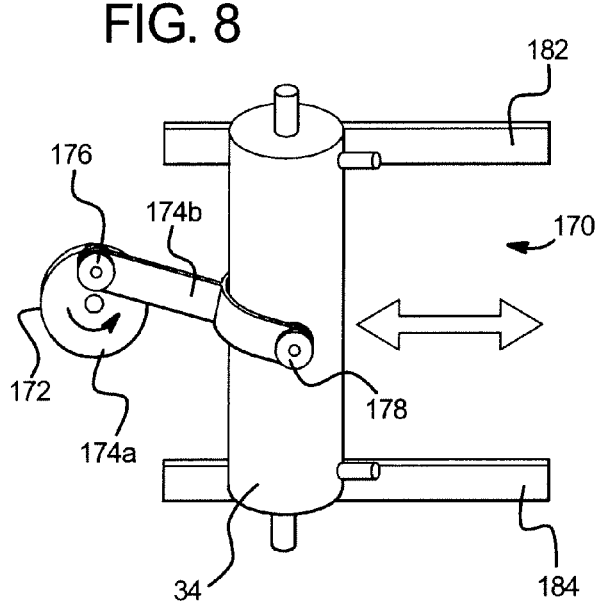
FIGS. 8 to 11 show various apparatuses for mechanically moving a dialyzer during prime.

FIG. 8 illustrates a first apparatus 170 for vibrating or moving dialyzer or filter 34. Apparatus 170 includes a motor 172, which can be an electric motor, such as an AC current, DC current, gear or stepper motor. Motor 172 in an alternative embodiment is operated by air. In any case, motor 172 is controlled by a motor controller, which can be a subornate controller to one or more master or higher level controllers. The motor controller (not illustrated) causes motor 172 to move in a single direction or in two directions either throughout the entire priming sequence or at selective times within the priming sequence.

A shaft of motor 172 is connected to a disk 174a that spins in a one to one relationship with the motor shaft. A reciprocating arm 174b is connected to rotating disk 174a via a pivoted connection 176. Reciprocating arm shaft 174b has a Y or wish bone shape, in which branches of shaft 174b split around dialyzer or filter 34 and connect to two sides of the dialzyer 34 via pivoted connections 178. Dialyzer or filter 34 can include pegs or protrusions that extend outwardly on two sides from the housing of dialyzer 34. The pegs or protrusions either snap-fit into pivoted connections 178 of shaft 174b. The Y branch of shaft 174b can be spread apart temporarily to enable the pivoted connections 178 to be snapped over the pegs or protrusions extending from dialyzer 34.

In one embodiment, dialyzer 34 is made with shaft 174b preinstalled. The installer of dialyzer 34 then snap-fits pivoted connection 176 to a similar peg or protrusion extending from disk 174*a*, which is premounted to the shaft of motor 172. In this embodiment, shaft 174*b* is provided with dialzyer 34, while disk 174*a* is made to be part of the instrument. Alternatively, shaft 174*b* is also made part of the instrument and is fitted to dialyzer 34 upon the installation of dialyzer 34 to a dialysis machine. Motor 172 can be located on either side of a dialyzer 34. Motor 172 can be located on either side of dialyzer 34.

Dialyzer 34 also includes pegs or protrusions (not illustrated) extending rearward towards the dialysis machine. These pegs or protrusions are located towards the top and bottom of dialyzer 34 and fit into tracks 182 and 184 formed in the dialysis machine. Tracks 182 and 184 can be formed along one of the sides of the dialysis machine or in front of the machine. In apparatus 170 of FIG. 8, tracks 182 and 184 are disposed horizontally. Motor 172 is coupled to dialyzer 34 such that shaft 174*b* is disposed generally horizontally or parallel to tracks 182 and 184, although pivoting end 176 of shaft 174*b* rotates up and down as disk 174*a* spins with the shaft of motor 172. Apparatus 170 accordingly causes dialyzer 34 to move horizontally back and forth within tracks 182 and 184. Tracks 182 and 184 are sized appropriately for the horizontal distance that the upper and lower pegs of dialyzer 34 travel when motor 172 spins, causing pivoted connection 176 to rotate about the motor shaft on disk 174 and in turn cause shaft 174*b* to push dialyzer 34 in one direction and pull dialyzer 34 in the opposite direction. Again, motor 172 can spin in one direction, in which dialyzer 34 travels in a longer horizontal cycle. Alternatively, motor 172 is toggled back and forth in two rotational directions, causing the horizontal motion of dialyzer 34 to have a shorter horizontal stroke, more akin to a vibration.

Figure 9:
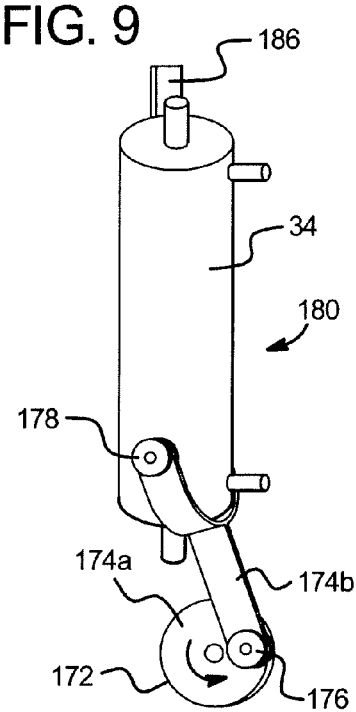

FIG. 9 illustrates an alternative priming agitator apparatus 180. Apparatus 180 includes many of the same features as apparatus 170, including dialyzer 34 connected pivotally at pivot connection 178 to a shaft 174*b*, which is connected pivotally at its opposite end 176 to a spinning disk 174*a* connected to a shaft of motor 172. Each of the alternative embodiments for motor 172 and the connection of shaft 174*b* to dialyzer 34 and disk 174*a* described above in connection with apparatus 170 of FIG. 8 is also applicable to system 180.

System 180 moves dialyzer 34 alternatively vertically within a vertically disposed slot 186. Here again upper and lower pegs (not illustrated) extend rearwardly from dialyzer of filter 34 and into vertically disposed track 186. Track 186 is sized appropriately for the total stroke length of dialyzer 34. Motor 172 is mounted below (as illustrated) or above dialyzer 34 such that the primary force vector of shaft 174*b* is vertical, whereas primary force vector of shaft 174*b* in FIG. 8 is horizontal.

As with system 170, motor 172 in system 180 can operate in a single rotational direction or toggle back and forth clockwise and counterclockwise to produce a longer vertical stroke (single direction) or short vertical stroke (bi-directional), more akin to a vibrating motion. Slot 186, motor 172 and disk 174*a* are again provided on or with the dialysis instrument or machine. Shaft 174*b* can be part of the instrument or provided with dialyzer or filter 34. Because the saline primes in a substantially vertical direction within dialyzer 34 when the dialyzer is mounted vertically as shown, it is believed that shaking or agitating dialyzer 34 in a vertical direction in system 180 may be more effective than the horizontal shaking or agitating of system 170. In either case, the agitation helps to release or shear air bubbles off the dialyzer fibers and inner surface of dialyzer 34.

Figure 10:
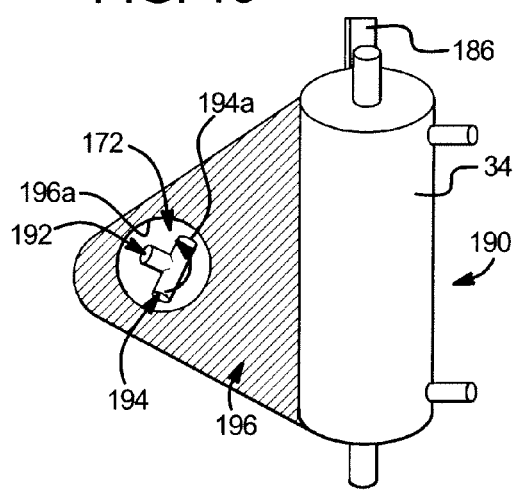

Referring now to FIG. 10, apparatus 90 illustrates an additional alternative priming agitator. Here, motor shaft 192 is connected to an unbalanced load 194, which is slidably coupled to a circular edge 196*a* of an aperture formed in a plate 196, which in turn is coupled to dialyzer or filter 34. Unbalanced load 194 can have a t-shape as shown in FIG. 10. Dialyzer 34 can have a single peg (not illustrated), which extends rearwardly into a vertical slot 186. Here, unbalance load 194 is rotated in a circular manner, such that at least one tip 194*a* of load 194 engages circular surface 196*a* and moves or agitates filter 34 in both a pivoting motion about the peg projecting from dialyzer 34 and also in a translational motion, pulling dialyzer 34 up and down within vertical slot 186. Motor 172 as before can pivot unbalance load 194 in a single direction or bi-directionally.

Plate 196 in an embodiment is a disposable piece mounted or formed with the housing of dialyzer 34. Plate 196 is alternatively a reusable piece that dialyzer 34 is mounted to during loading. Dialyzer 34 when mounted to the dialysis instrument is disposed such that aperture 196*a* fits over load 194, such that edge 196*a* of the aperture comes into contact with load and 194*a*.

Figure 11:
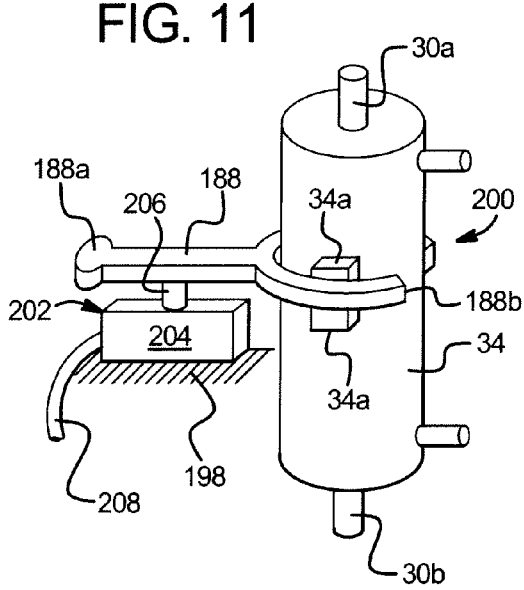

Referring now to FIG. 11, apparatus 200 illustrates a further alternative agitator usable for priming dialzyer 34 and associated arterial line 30*a* and venous line 30*b* of the extracorporeal circuits. Here, a dialyzer holding arm 188 is attached in a vertically movable configuration to the dialysis instrument or machine (not shown). For example, arm 188 can terminate with a slidable bearing 188*a*, which fits inside a cylindrical track in the dialysis machine. The opposite end 188*b* of arm 188 snap-fits around the body of dialyzer 34. Shaft 188 is supported by a vibrator 202, which has a body 204 mounted to a surface 198 of the dialysis machine. Vibrator 202 includes a head 206 that vibrates in and out of body 204. Head 206 of vibrator 202 in an embodiment is coupled physically to arm 188 holding dialyzer 34. Dialyzer 34 can have tabs 34*a*, which snap-ring 188*b* of arm 188 pushes against in the direction to move dialyzer 34.

Vibrator 202 is alternatively an ultrasonic vibrator, which imparts ultrasonic vibrations to arm 188 or directly to filter 34. Further alternatively, the sound vibrations may be imparted to the dialysate traveling in arterial line 30*a*, upstream of filter 34.

An air line 208 is connected sealingly to body 204 to provide pressurized air to vibrator 202. One suitable miniature air piston vibrator 202 for apparatus 200 is provided by Cleveland Vibrator Co., Cleveland, Ohio, part no. VN-25. An ultrasonic vibrator may be used alternatively. In either case, vibrator 202 causes arm 188 and dialyzer 34 to vibrate vertically, which is believed to be advantageous as discussed above.

Disposable Fluid Sprayer for Removal of Dissolved Gases

Figure 12:
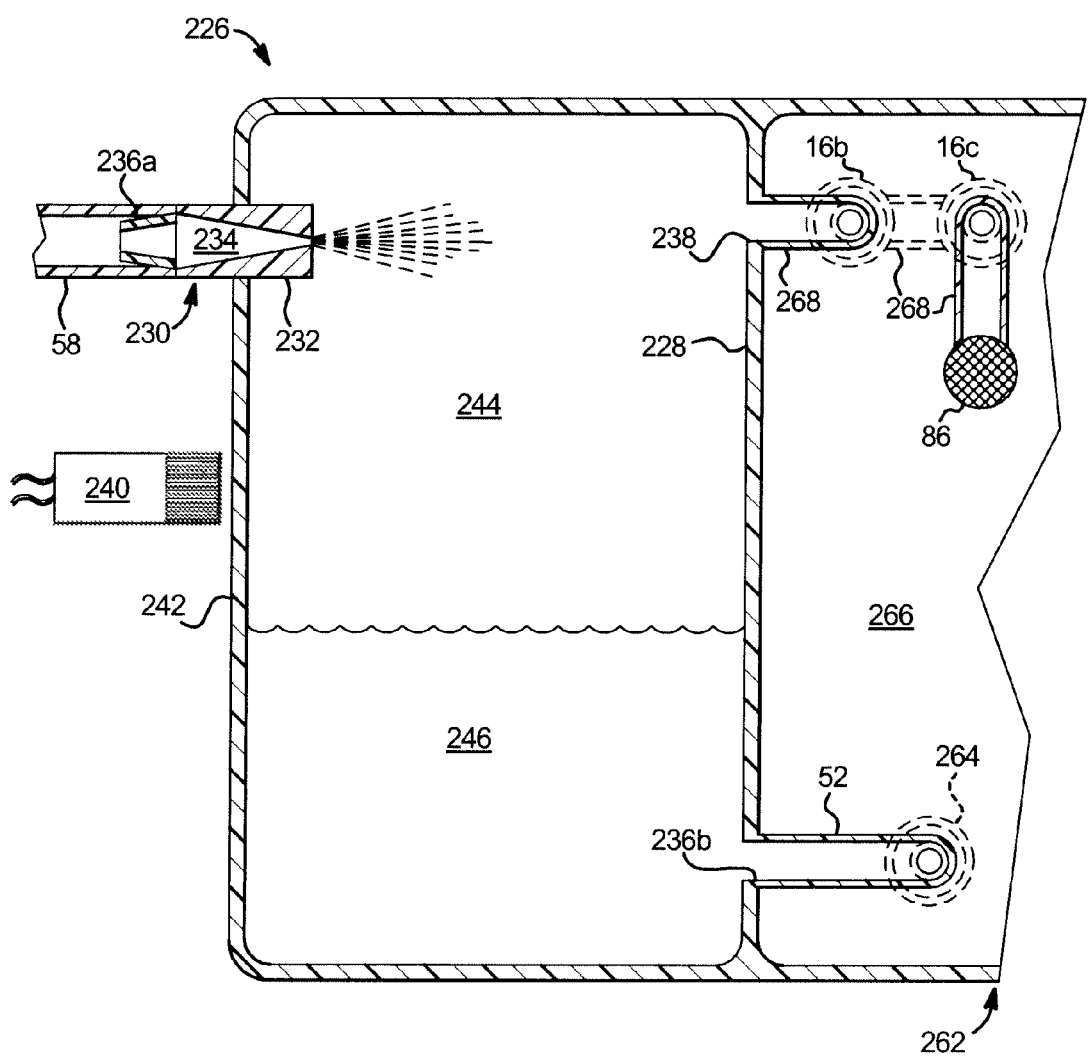
FIG. 12 is a sectioned elevation view of a disposable cassettes that includes an air trap having a spray nozzle configured to transform fresh solution into a spray for air removal.

Referring now to FIG. 12, a system and method for removing gas, e.g., air, from dialysate is illustrated. It should be appreciated that the apparatus and method of FIG. 12 are applicable to any renal failure therapy treatment, such as any kind of blood treatment or peritoneal dialysis treatment. Accordingly, the term dialysate is used in at least this section includes dialysate for hemodialysis, dialysate for peritoneal dialysis, and infusate or replacement fluid for hemofiltration. Any of these fluids can have entrapped air. The air needs to be removed from the fluid before the fluid is delivered to the patient. Air separation device 226 shown in FIG. 12 can be used in place of dialysate air trap 26 shown in FIGS. 1 and 7 or in place of either of air traps 26 shown in FIG. 6. All other apparatus discussed in connection with those figures, including all alternative embodiments thereof, are assumed to be present in the system and method of FIG. 12. For convenience, only air trap 226 and surrounding structure are shown in FIG. 12.

It is expressly contemplated to provide air trap 226 in combination with or as part of a disposable cassette, shown here as disposable pumping cassette 262. A rigid wall 228 of air trap 226 separates the air trap from the remainder of disposable pumping cassette 262. Dialysate inlet line 52 is shown exiting the bottom of air trap 226 from wall 228. Here, dialysate inlet line 52 is a rigid flowpath of cassette 262, which extends from an outlet 236b of air trap 226 and to a valve chamber 264 of cassette 262, located on an opposite side of a rigid wall 266 from flowpath 52. Dialysate pumps 18a and 18b can be diaphragm pumps, which use flexible sheeting on cassette 262 to suck dialysate fluid in and push dialysate fluid out of cassette 262. Here, valve 264 could be an inlet valve to a diaphragm pump located on the same side of base wall 266 as valve 264.

Alternatively, as seen in FIG. 1 flowpath 52 flows from the air trap to a peristaltic pump. In the alternative embodiment, rigid pathway 52 extends to a port located at a side or edge of cassette 226, wherein the port is connected to a tube running for example to peristaltic pump 18a shown in FIG. 1. FIG. 12 also shows a level detector 240 operable with air trap 226. Level detector 240 senses whether a liquid level has reached a point at which liquid needs to be removed from air trap 226 for safe operation of the system.

Air trap 226 includes an air duct 238, which communicates fluidly with a rigid air vent line 268 formed on the same side of base wall 266 as rigid flowpath 52. Air duct 238 extends to both sides of wall 266 for valved operation. Vent valves 16b and 16c are pneumatically controlled valves in one embodiment that selectively allow air to be vented through filter 86 located on the same side of base wall 266 as flowpaths 52 and 268. Valve chambers 16b and 16c are located on the same side of base wall 266 as valve chamber 264 (both in phantom line) in the illustrated embodiment.

Cassette 262 in FIG. 12 is shown in one preferred operable mounting position having inlet 236a of air trap 226 located elevationally above the fluid outlet 236b of air trap 226. A nozzle 230 is formed in or connected to a sidewall 242 of air trap 226 of cassette 262. Nozzle 230 in an embodiment includes a nozzle body 232, which is shaped, e.g., narrowing in a linear fashion to form a nozzle aperture 234. Nozzle aperture 234 is shaped and configured to accept fresh dialysate from a supply line 58, which is shown in FIG. 1 extending from a heater 22. A second fresh pump 18a can be located upstream of air trap 26 if needed to pressurize the dialysate ahead of the nozzle. The pressure necessary to produce a desired spray should be provided by the nozzle manufacturer if nozzle 230 is as an off-the-shelf component. Otherwise, a pressure of about 500 to about 600 mmHg may be a suitable upstream pressure range.

Nozzle 230 atomizes or causes the dialysate to form a mist, which exits body 232 of nozzle 230, into an air separation portion 244 of air trap 226. The atomization increases the surface area of dialysate exposed to air in air removal area 244. A local negative pressure caused by downstream fresh pump 18a helps to remove gas from the mist. The fluid mist strikes the wall of the chamber or falls naturally into a pool 246 of the degassed fresh dialysate. Downstream fresh dialysate pump 18a pumps the pooled, degassed dialysate to the patient. It is advantageous in one embodiment to heat the dialysate before it reaches nozzle 230, because raising the temperature of dialysate reduces gas solubility of the dialysate.

Non-disruptive Patient Alert Dialysis System

Figure 13:
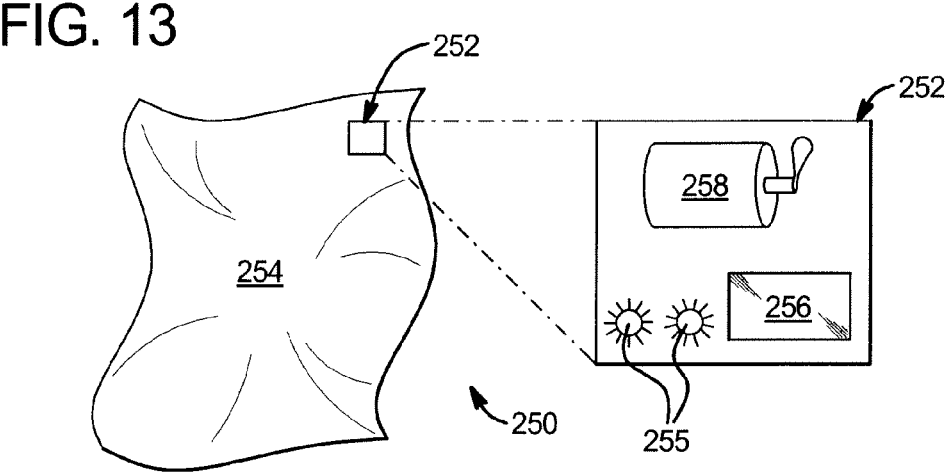
FIGS. 13 to 15 show various patient alarm embodiments.
Figure 14:
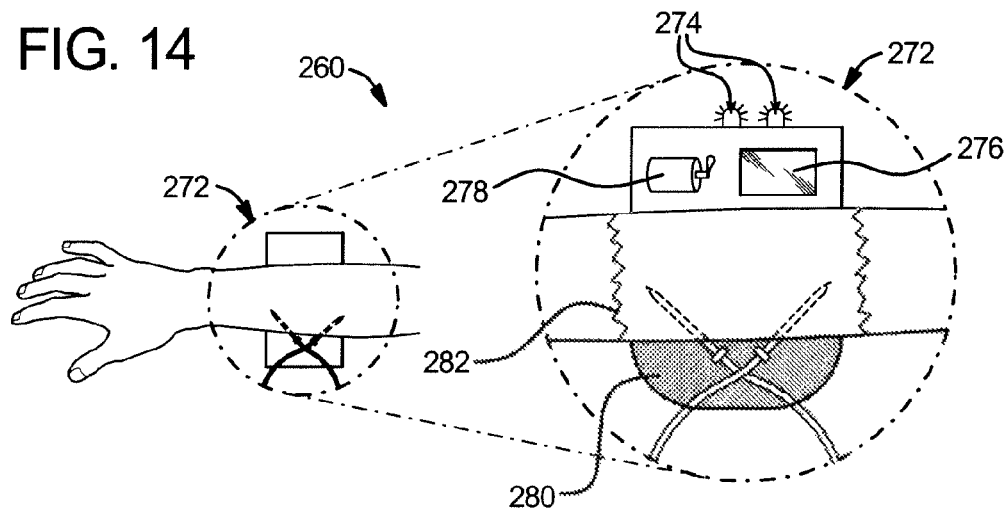
Figure 15:
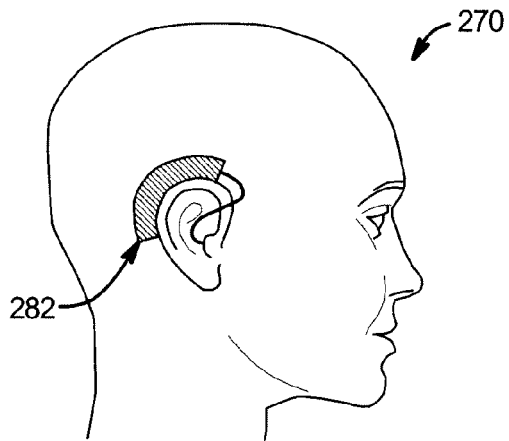

Referring now to FIGS. 13 to 15, systems 250, 260 and 270 show several systems and methods for a non-disruptive patient or caregiver alert. Any of the systems described herein can be subject to a plurality of alarm or alert conditions. For example, the non-invasive flow systems can experience a low-flow or no-flow condition. The primary systems may experience a system integrity or fluid leak condition. Any system described herein can alarm if air is discovered. In any of the alarm conditions, the dialysis instrument typically alerts the patient and may terminate therapy. In a no-flow or low-flow situation, the instrument may try to remove an occlusion to eliminate the condition. In any case, it is likely necessary that the machine will alert the patient, nurse, spouse, friend or caregiver of the situation. In a nighttime therapy it is desirable to alert only the person that needs to be alerted, so as not to wake a spouse or other patient for example. The systems described herein adhere this need.

System 250 of FIG. 13 shows a small electromechanical device 252 embedded into a patient blanket 254. The patient uses blanket 254 to keep warm while the therapy is underway. Alternatively, device 252 could be pulled from the blanket 254 and placed in another convenient location for the patient, such as under the patient's pillow or attached directly to the patient's clothing or skin. Device 252 includes several visual indicator lights 255 and/or a small video display 256 as well as small electric motor or vibrator 258, e.g., ultrasonic vibrator, that can vibrate to capture the patient's attention in an alarm condition. The communications link between device 252 and the main extracorporeal therapy machine is either a wired hard line, or a wireless connection (such as Bluetooth™, infrared, 802.11, Zigbee-802.15.4 wireless technology).

System 260 of FIG. 14 shows an alternative device 272 that is configured to be placed directly on the patient using a bandage, harness or strap 282 to hold device 272 in place. In FIG. 14, alert device 272 includes several visual indicator lights 274 and/or a video screen 276 and a small electric motor or vibrator 278 that can vibrate to capture the patient's attention. Device 272 can be integrated into the same bandage, harness or strap 282 that is used with the access site on the patient's arm, allowing device 272 to also house an access disconnect sensing ("ADS") system 280 located directly on the patient's arm. Device 272 is attached alternatively elsewhere on the patient's body which does not incorporate ADS system 280. The communication link between device 272 and ADS system 280 (or just alert device 272) and the main extracorporeal therapy machine could be via any of the technologies discussed above for system 250.

System 270 of FIG. 15 shows a device 282 that can be worn on or in the patient's ear, akin to a hearing aid or hands-free telephone device. Device 282 in one embodiment includes a vibrating alert and/or an auditory alert that is set at a level only audible to the patient because of the proximity of device 282 to the patient's ear. The link between device 282 and the main extracorporeal therapy machine could be any of the technologies discussed above for system 250.

It is contemplated that a nurse or caregiver alternatively wear device 282 either at the nurse's ear or elsewhere adjacent to the nurse's body. The nurse could use a single device 282, which is programmed alternatively to respond to attention requests from any of several separate machines. For example, a nurse or training individual that is responsible for the operation of several machines on several patients could wear device 282, which would alert the nurse when attention is required. It is farther contemplated to equip the device with a display that tells the nurse which machine and patient requires attention, and possibly the type of attention required.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A renal treatment fluid priming method comprising:
priming an extracorporeal circuit connected to a patient with a physiologically compatible fluid, the extracorporeal circuit including an arterial line, a venous line and blood compartment of a blood filter; and
pumping from a renal treatment fluid line in communication with the blood filter (i) pulling blood from the patient through the arterial line to flush the physiologically compatible fluid through the arterial line and the blood filter compartment into the renal treatment fluid line and (ii) pulling blood from the patient through the venous line to flush the physiologically compatible fluid through the venous line and the blood filter compartment into the renal treatment fluid line,
such that a greater volume of blood is pulled from the patient via (i) and (ii) than a volume of the extracorporeal circuit.

2. The priming method of claim 1, wherein the physiologically compatible fluid includes saline, and which includes pumping one of dialysate and infusate in the renal treatment fluid line initially to perform (i) or (ii).

3. The priming method of claim 1, wherein the physiologically compatible fluid includes one of dialysate and infusate.

4. The priming method of claim 1, which includes flushing the physiologically compatible fluid through the blood filter compartment to a drain.

5. The priming method of claim 1, which includes flushing the physiologically compatible fluid through the blood filter compartment through pores formed in membranes located in the blood filter.

6. The priming method of claim 1, which includes additionally using an extracorporeal circuit pump to flush the physiologically compatible fluid from at least one of the arterial and venous lines.

7. The priming method of claim 1, which includes using a return line pump in the renal treatment fluid line to flush the physiologically compatible fluid from at least one of the arterial and venous lines.

8. The priming method of claim 7, wherein the return line pump is a drain line pump.

9. The priming method of claim 1, which includes priming the renal treatment fluid line with renal treatment fluid prior to the replacing steps.

10. The priming method of claim 1, which includes performing at least one of (i) and (ii) over a predetermined number of pump strokes.

11. The priming method of claim 1, which includes at least one of (i) closing a valve in the venous line when flushing the physiologically safe fluid through the arterial line; and (ii) closing a valve in the arterial line when flushing the physiologically safe fluid through the venous line.

12. The priming method of claim 11, which includes positioning the valve in the venous or arterial line near the filter.

13. The priming method of claim 1, which includes performing (i) and (ii) simultaneously.

14. A renal treatment fluid priming method comprising:
priming an extracorporeal circuit connected to a patient with a physiologically compatible fluid, the extracorporeal circuit including an arterial line, a venous line and blood compartment of a blood filter; and
pumping from the extracorporeal circuit to (i) pull blood from the patient through the arterial line to flush the physiologically compatible fluid through the arterial line and the blood filter compartment into a renal treatment fluid line and (ii) pull blood from the patient through the venous line to flush the physiologically compatible fluid through the venous line and the blood filter compartment into the renal treatment fluid line,
such that a greater volume of blood is pulled from the patient via (i) and (ii) than a volume of the extracorporeal circuit.

15. The priming method of claim 14, wherein the physiologically compatible fluid includes one of saline, dialysate and infusate.

16. The priming method of claim 14, which includes flushing the physiologically compatible fluid through the blood filter compartment to a drain.

17. The priming method of claim 14, which includes flushing the physiologically compatible fluid through the blood filter compartment through pores formed in membranes located in the blood filter.

18. The priming method of claim 14, which includes additionally using dialysate circuit pump to flush the physiologically compatible fluid from at least one of the arterial and venous lines.

19. The priming method of claim 14, which includes additionally using a return line pump in the renal treatment fluid line to flush the physiologically compatible fluid from at least one of the arterial and venous lines.

20. The priming method of claim 14, which includes priming the renal treatment fluid line with renal treatment fluid prior to the replacing steps.

21. The priming method of claim 14, which includes performing at least one of (i) and (ii) over a predetermined number of pump strokes.

22. The priming method of claim 14, which includes at least one of (i) closing a valve in the venous line when flushing the physiologically safe fluid through the arterial line; and (ii) closing a valve in the arterial line when flushing the physiologically safe fluid through the venous line.

23. The priming method of claim 14, which includes performing (i) and (ii) simultaneously.

* * * * *